US009078565B2

(12) United States Patent
Profio et al.

(10) Patent No.: US 9,078,565 B2
(45) Date of Patent: *Jul. 14, 2015

(54) DUAL DISPLAY CT SCANNER USER INTERFACE

(71) Applicant: General Electric Company, Schenectady, NY (US)

(72) Inventors: Mark Vincent Profio, Elm Grove, WI (US); Holly Ann McDaniel, Waukesha, WI (US); Cheryl Ruth Jones, Hubertus, WI (US); Tabb Alan Patz, New Berlin, WI (US); Megan Elizabeth Wimmer, Milwaukee, WI (US); Amanda Jean Fox, Fox Point, WI (US); Jon V. Wettersten, Chicago, IL (US); Simon J. King, Chicago, IL (US); Stina Maria Jonsson, Chicago, IL (US)

(73) Assignee: General Electric Company, Schenectady, NY (US)

( * ) Notice: Subject to any disclaimer, the term of this patent is extended or adjusted under 35 U.S.C. 154(b) by 226 days.

This patent is subject to a terminal disclaimer.

(21) Appl. No.: 13/644,695

(22) Filed: Oct. 4, 2012

(65) Prior Publication Data

US 2014/0098931 A1 Apr. 10, 2014

(51) Int. Cl.
*G06K 9/00* (2006.01)
*A61B 6/03* (2006.01)
*A61B 6/00* (2006.01)
*A61B 8/00* (2006.01)
*G06F 19/00* (2011.01)
*G09G 5/00* (2006.01)

(52) U.S. Cl.
CPC . *A61B 6/03* (2013.01); *A61B 6/032* (2013.01); *A61B 6/463* (2013.01); *A61B 6/464* (2013.01); *A61B 6/465* (2013.01); *A61B 8/54* (2013.01); *G06F 19/3406* (2013.01); *G09G 5/00* (2013.01); *A61B 6/468* (2013.01); *A61B 6/469* (2013.01); *A61B 6/481* (2013.01); *A61B 6/488* (2013.01); *A61B 6/504* (2013.01); *A61B 6/5294* (2013.01); *A61B 6/541* (2013.01)

(58) Field of Classification Search
USPC .......................................................... 378/98
See application file for complete search history.

(56) References Cited

U.S. PATENT DOCUMENTS

| 7,031,423 | B2 | 4/2006 | Tsukagoshi |
| 7,613,672 | B2 | 11/2009 | West et al. |
| 7,929,740 | B2 * | 4/2011 | Marshall et al. ............... 382/128 |
| 7,970,634 | B2 | 6/2011 | Backhaus et al. |
| 7,979,378 | B2 | 7/2011 | West et al. |
| 2007/0214017 | A1 | 9/2007 | Profio et al. |

(Continued)

*Primary Examiner* — Phillip A Johnston
(74) *Attorney, Agent, or Firm* — Ziolkowski Patent Solutions Group, SC

(57) ABSTRACT

A user interface for a CT imaging system is disclosed. The user interface includes a first display configured to enable an operator to perform set-up and scanning tasks associated with performing a CT exam on one or more patients, with the set-up and scanning tasks including acquiring and verifying scan image data. The user interface also includes a second display configured to enable the operator to perform image post-processing tasks associated with the CT exams on the one or more patients, with the image post-processing tasks including performing image reconstructions and reformats. Each of the first display and the second display are operable independent from one another to provide for parallel workflows between the first display and second display and between the patient set-up and scanning tasks and the post-processing tasks.

19 Claims, 22 Drawing Sheets

(56) References Cited

U.S. PATENT DOCUMENTS

| | | | |
|---|---|---|---|
| 2007/0238963 A1* | 10/2007 | Kaminaga et al. | 600/407 |
| 2008/0119717 A1 | 5/2008 | Profio et al. | |
| 2008/0120284 A1 | 5/2008 | Profio et al. | |
| 2009/0213034 A1* | 8/2009 | Wu et al. | 345/1.1 |
| 2012/0014499 A1 | 1/2012 | Feuerlein et al. | |

* cited by examiner

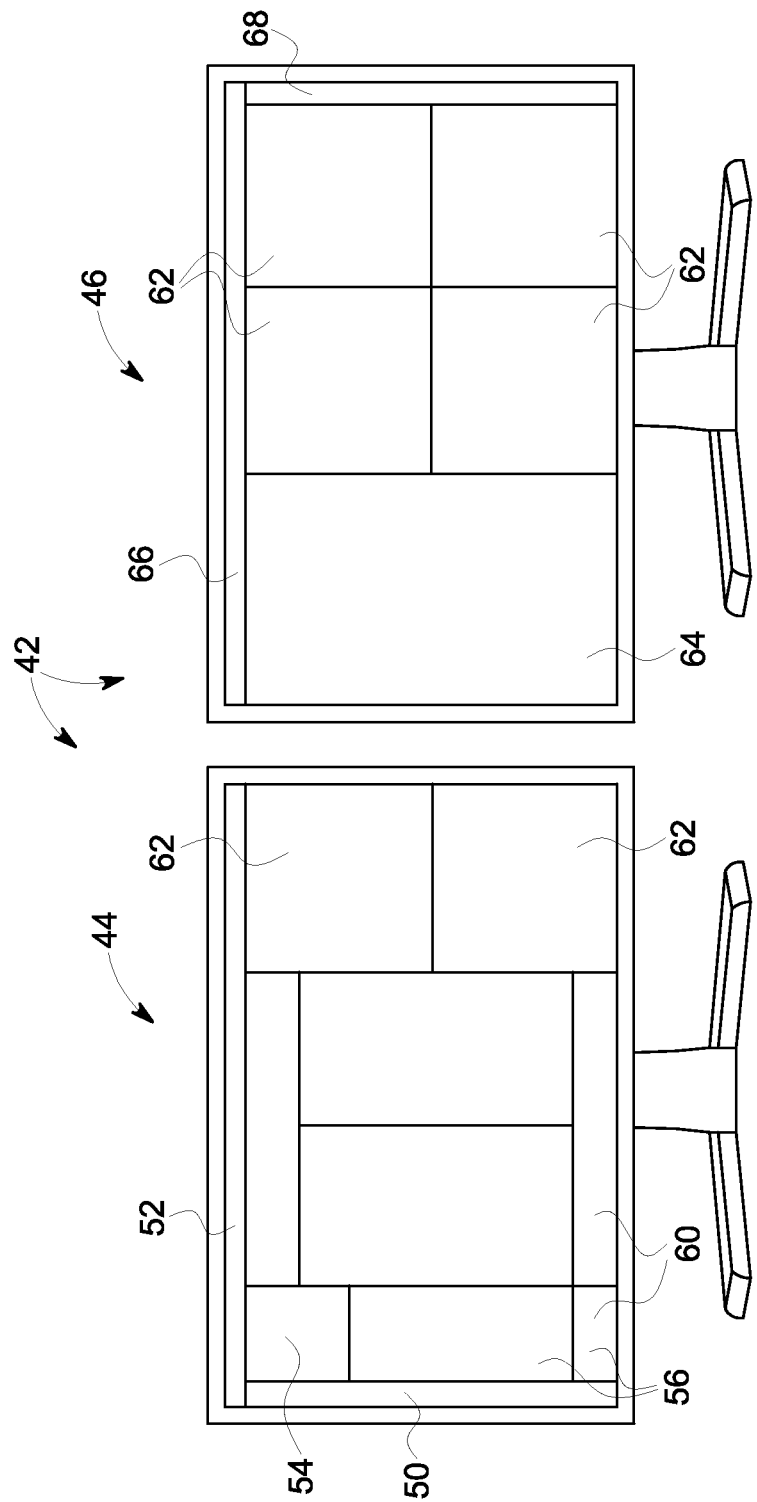

FIG. 4

| NAME | PATIENT ID | ACCESSION NO. | EXAM | DATE | TIME | STATUS | DEL |
|---|---|---|---|---|---|---|---|
| Wendy Krause | 054-42-4544 | 2328-37863-22 | C-Spine | 07/07/10 | 13:30 | N | x |
| Jackie Huff | 984-49-2746 | 9854-49274-61 | Head and Chest Trauma | 07/07/10 | 14:30 | N | x |
| Wanda Ha | 804-98-1827 | 8064-98182-97 | Facial Bones | 07/07/10 | 15:30 | N | x |
| Cynthia Haig | 232-83-7863 | 4543-97657-00 | Aortic Dissection | 07/07/10 | 16:30 | N | x |
| Lori Taylor | 789-78-0991 | 1849-74809-91 | Shoulder | 07/07/10 | 18:15 | N | x |
| Jonathan Moore | 400-89-067 | 8374-623-81 | Abd / Chest Abd Pelvis (with) | 07/07/10 | 19:30 | N | x |
| Suzy Armstrong | 938-00-3837 | 1273-69872-82 | Routine Head | 07/08/10 | 08:30 | C | x |
| Tad Wells | 736-37-9872 | 4540-54245-44 | Chest / ABD / Pelvis | 07/08/10 | 09:45 | C | x |
| Helen Peterson | 054-42-4544 | 3298-44927-46 | Abdomen | 07/08/10 | 11:40 | C | x |
| Akira Shamaoka | 984-49-2746 | 4575-38049-81 | Pelvis | 07/08/10 | 15:30 | C | x |
| Conrad Busse | 804-98-1827 | 2099-32865-97 | Routine Chest with Contrast | 07/08/10 | 19:00 | C | x |
| Mae Woodman | 232-83-7863 | 4322-97645-82 | Head with Contrast | 07/08/10 | 22:00 | C | x |
| Robert Sullivan | 659-43-9765 | 9338-38379-76 | Routine Head | 07/09/10 | 09:30 | C | x |

+ SELECT PATIENT

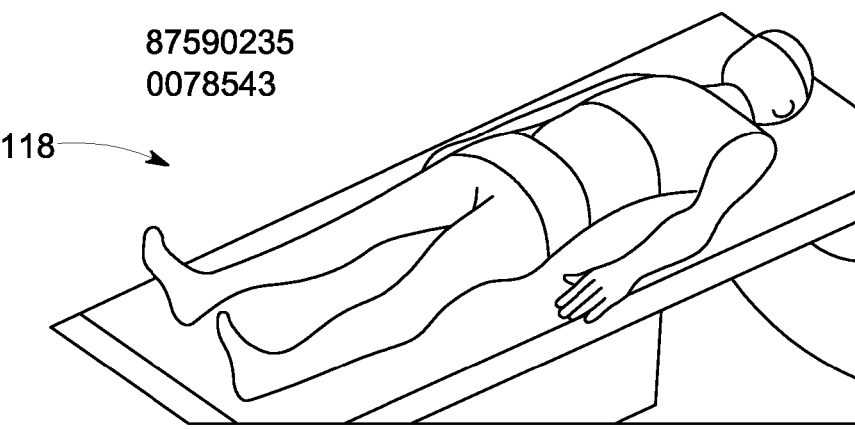
Jonathan Moore
87590235
0078543
118
PATIENT
| | |
|---|---|
| Landmark reference | OM |
| Patient Orientation | Head First |
| ✔ Inherit orientation from most recent scan series. | |
| Patient Position | Supine |
| Inherit Position from most recent scan series. | |
| Auto Voice Language | English |
| Preset Load Position | Yes |
| Clinical Application ID | ONC |
120
FIG. 7

POST PROCESSING
Jonathan Moore

| SCAN SERIES 1 | RECON SETTINGS |
|---|---|
| * Soft Tissue 5.000mm | RECON OPTIONS<br>Bone / Plus / 400 / 40 / None |
| Coronal | ANATOMY SELECTION |
| (Custom Identifier) | Start — S0.00<br>End — 1200.00 |
| 3D Volume | Number of Images — 641<br>SFOV — Large Body |
| * Soft Tissue 5.000mm | DFOV — 36.0 |
| Bone 5.000mm | A/P — A0.0<br>L/R — L0.0 |
| Lung .625mm | OUTPUT OPTIONS / ACCESSION #<br>Film / Auto-Display / 4564561(Chest Ab..) |
| Coronal | CUSTOM ID<br>Name |
| | TRANSFER<br>✓ USB   ✓ Host 3<br>✓ Host 1   ⊘ Host 4<br>→ Host 2   Other ▼ |
| | [DELETE RECON] |
| 231 | 234 |

DUAL DISPLAY CT SCANNER USER INTERFACE

BACKGROUND OF THE INVENTION

Embodiments of the invention relate generally to computed tomography (CT) imaging and, more particularly, to a CT user interface configured to enable multi-tasking workflow, collaboration, multiple throughput use cases, and consistency in scan quality.

Typically, in computed tomography (CT) imaging systems, an x-ray source emits a fan-shaped beam toward a subject or object, such as a patient or a piece of luggage. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. The outputs of the photodiodes are then transmitted to the data processing system for image reconstruction.

It is well recognized that CT scanner technology is growing increasingly complex and capable as innovations in electronics, computing, and imaging physics enable both new clinical applications and bring what were considered boutique and difficult CT examinations into the realm of a routine case. In keeping with such advancements in CT scanner technology, the design of CT scanner user interfaces has also evolved in order to add new capabilities addressing such new clinical applications. However, in evolving to keep pace with advances in technology, little thought has been given to CT scanner user interface design with respect to addressing actual working conditions and customer needs. Accordingly, existing CT scanner UI designs posses a linear, sequential architecture, and become consumed with system tasks, such as post-processing, thereby causing long bottlenecks that reduces the overall efficiency of the CT scanner. Existing CT scanner UI designs also fail to properly identify the users involved at different points in the patient experience with a CT study and lack a clear presentation and prioritized design framework supporting the fundamental workflow of a patient CT exam, which progresses as: Setup Exam>Customize Preferences>Adjust for Patient>Capture & Evaluate>Create Final Images>Finish.

Therefore, it would be desirable to design a CT scanner UI that addresses issues including multi-tasking workflow, collaboration, multiple throughput use cases, and consistency in scan quality.

BRIEF DESCRIPTION OF THE INVENTION

Embodiments of the invention are directed to a CT user interface configured to enable multi-tasking workflow, collaboration, multiple throughput use cases, and consistency in scan quality.

In accordance with one aspect of the invention, a user interface for a CT imaging system includes a first display configured to enable an operator to perform set-up and scanning tasks associated with performing a CT exam on one or more patients, with the set-up and scanning tasks including acquiring and verifying scan image data. The user interface also includes a second display configured to enable the operator to perform image post-processing tasks associated with the CT exams on the one or more patients, with the image post-processing tasks including performing image reconstructions and reformats. Each of the first display and the second display are operable independent from one another to provide for parallel workflows between the first display and second display and between the patient set-up and scanning tasks and the post-processing tasks.

In accordance with another aspect of the invention, a user interface for a CT imaging system includes a first display configured to enable an operator to perform set-up and scanning tasks associated with performing a CT exam on one or more patients and a second display configured to enable the operator to perform image post-processing tasks associated with the CT exams on the one or more patients. Each of the first display and the second display are configured to display a plurality of distinct display zones thereon, with the plurality of display zones including a tabs zone on the first display comprising a plurality of tabs each directed to a distinct subject, wherein selection of one of the plurality of tabs by the operator causes subject specific and scan specific information to be displayed on the first and second displays. The plurality of display zones also includes a task list zone on the first display that is configured to display all steps in a CT scan for a subject selected via a tab in the tabs zone and enable operator selection of a particular step, settings and scanning zones on the first display that are configured to display the subject specific and scan specific information for a respective subject whose tab is selected and a respective step selected in the task list zone, and a post-processing zone on the second display that is configured to enable the operator to manage post-processing set-up, monitoring, and transferring tasks for a CT scan that has been performed. The plurality of distinct display zones on the first and second displays enable the operator to perform workflows on multiple subjects and enable simultaneous usage of the first display and the second display by multiple operators.

In accordance with yet another aspect of the invention, a CT imaging system includes a rotatable gantry having a gantry opening to receive a subject to be scanned, a high frequency electromagnetic energy projection source configured to project a high frequency electromagnetic energy beam toward the subject, a detector array configured to detect high frequency electromagnetic energy passing through the subject and generate a detector output responsive thereto, a data acquisition system (DAS) connected to the detector array and configured to receive the detector output, and an image reconstructor connected to the DAS and configured to reconstruct one or more images of the subject from the detector output received by the DAS. The CT imaging system also includes a user interface configured to be usable by an operator to set scan related parameters and perform scan related tasks and observe the one or more reconstructed images generated by the image reconstructor, with the user interface further including a first display configured to enable the operator to perform set-up and scanning tasks for one or more patients including acquiring and verifying scan image data and a second display configured to enable the operator to perform image post-processing tasks including reconstructions and reformats. Each of the first display and the second display are configured to display a plurality of distinct display zones thereon, with each of the plurality of display zones being dedicated to a specified task associated with a CT scanning process of the subjects.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings:

FIG. 3 is an illustration of a dual display user interface of the CT imaging system illustrated in FIG. 1.

FIG. 4 is an illustration of a patient scheduler zone on the dual display user interface of FIG. 3.

FIG. 7 is an illustration of a patient area zone on the dual display user interface of FIG. 3.

FIGS. 17A-17C are illustrations of an Edit Settings Panel, DPMR application, and AW application, for selective display in a portion of the post-processing zone of FIG. 16.

FIG. 18 is an illustration of a file manager zone on the dual display user interface of FIG. 3.

DETAILED DESCRIPTION OF THE PREFERRED EMBODIMENT

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
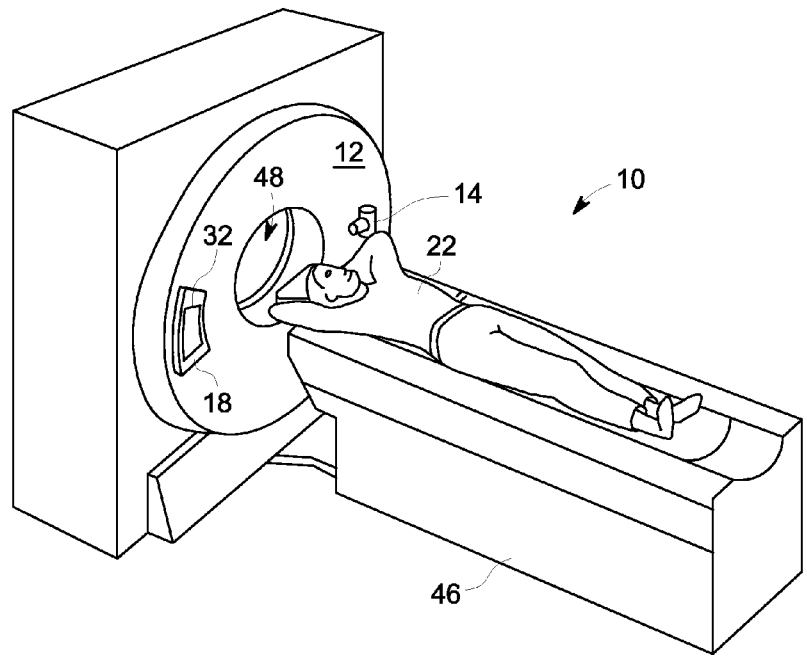
FIG. 1 is a pictorial view of a CT imaging system.
Figure 2:
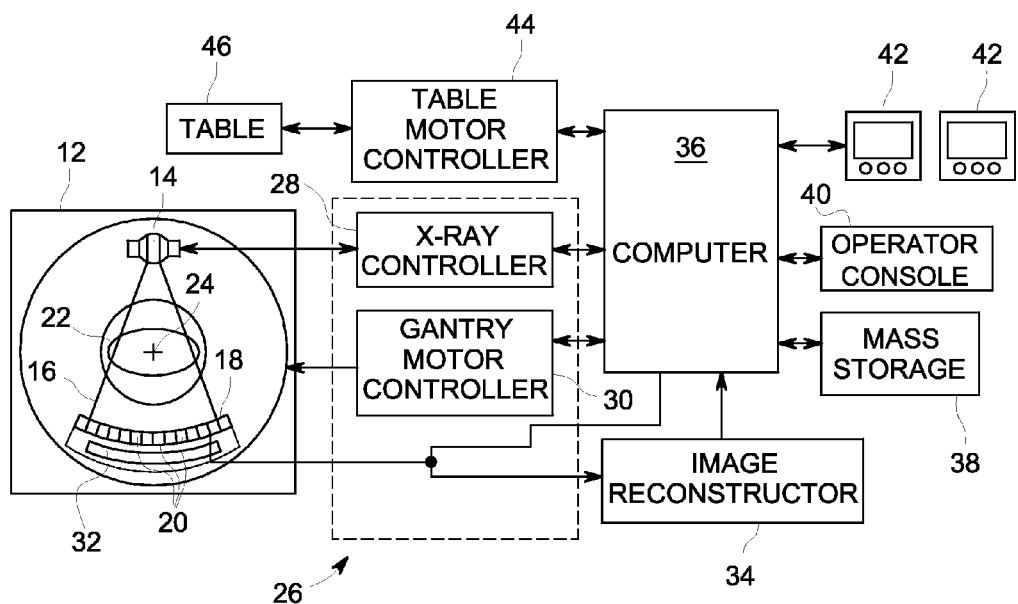
FIG. 2 is a block schematic diagram of the CT imaging system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 and user interface 42, with the console and user interface having some form of operator interface, such as a keyboard, mouse, voice activated controller, or any other suitable input apparatus and displays that allow the operator to set scan parameters and observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Referring now to FIG. 3, user interface 42 is shown in more detail according to an exemplary embodiment of the invention. The user interface 42 is configured as a dual display user interface that includes a left display 44 and a right display 46. The left display 44 is dedicated to setting up a new patient and scanning, which includes setting-up a new patient to scan and acquiring and verifying the scan image data. The right display 46 is dedicated to post-processing, viewing, and management of previously done exams and serves as a dashboard of reconstructions and reformats that the technologist can glance at to determine and verify what processes are configured, started, need attention, completed, or have been transferred. The distinct left and right displays 44, 46 beneficially allow for components needed to complete a task (whether acquiring a Scout or Reformatting images, for example) to be grouped together and kept on one display, so as to display useful information at the right time in the right place. Additionally, the distinct left and right displays 44, 46 enable collaboration between a technician and other colleagues, as these intervening colleagues can use the right display to view images while allowing the technologist to proceed with her scanning on the left display, for example. The user interface 42 thus provides a departure from the linear, sequential architecture of typical prior art user interfaces, enabling multi-tasking and collaboration between personnel, while still providing a clear navigation structure with tools and components at each step that direct, guide, and support technologists throughout an exam and providing the flexibility to accommodate situational factors such inserting an emergency scan or receiving a phone call from a radiologist requiring additional images.

As shown in FIG. 3, each of the left and right displays 44, 46 includes a plurality of clearly defined spatial zones, with each spatial zone having a unique identity to provide a consistent place for a technologist to perform specific steps. The defined spatial zones on the left and right displays 44, 46 include: a patient scheduler zone 50, a tabs zone 52, a patient area zone 54, a task list zone 56, a scout/settings/scanning zone 58, a dose area zone 60, viewport zones 62, a post-processing zone 64, a status zone 66, and a file manager zone 68. The design and layout of the zones 50-68 is based upon an understanding of the functional and emotional needs of technologists, with the positioning/arrangement of the zones 50-68 functioning to organize workflow activities within logical groupings on the left and right head displays so as to help technologists focus on a particular task and alleviating multitasking constraints. The architecture of user interface 42 and layout of the zones 50-68 support this focused attention and provide only the necessary tools and views that the technologist needs in order to perform certain activities, with unnecessary general user interface elements retreating to the background to simplify the user interface presented to the technologist.

Referring to FIG. 4, the patient scheduler zone 50 is shown in greater detail. The patient scheduler zone 50 is one of two "drawers" (the other is the file manager zone 68) within the user interface 42 that are consistently present in either a closed or open state. The patient scheduler zone 50 is located on the left display 44 and is anchored to the left side of the left display 44. As shown in FIG. 4, the patient scheduler zone 50 is expandable to an open state from the closed state to provide access to the data contained therein. Because the patient scheduler zone 50 is a feature associated with the display as a whole, and not a particular exam, it exists on a higher layer than any tabs in the tabs zone 52 that may be open. Access to the patient scheduler zone 50 is available at any point, quickly handling unexpected situations or checking on upcoming patients, to the technologist. Tasks enabled by the patient scheduler zone 50 are some of the first steps in any workflow, thus it is found on the left side of the left display 44 in order to reinforce the left-to-right workflow concept embodied by the architecture of CT user interface 42.

As shown in FIG. 4, the patient scheduler zone 50 includes a list of patients 70 that previously have been entered into the user interface 42 of the CT system. The patient scheduler zone 50 is used in different ways depending on the scanning institution. For this reason, columns of information corresponding to the patient list 70 can be sorted according to any of the following columns by clicking on their column header: Name 72, Patient ID 74, Accession No. 76, Exam 78, Date 80, Time 82, or Status 84. Additional features within the patient scheduler zone 50 include a Context Menu 86 that includes secondary functions such as "Add patient," "Delete all," "Preferences," and "Remove all completed exams" that are needed less frequently and therefore do not need to be visible at all times. Info Icons 88 can also be included in the patient scheduler zone 50 that display additional detailed information about the patient or the exam when clicked on, along with a Delete feature 90 to remove a patient from the Scheduler list when clicked, and a "Select Patient" button 92 that functions to create a new exam tab in tabs zone 52 (FIG. 3), as explained below, by double-clicking a patient name or highlighting a patient within the Scheduler list 70 and clicking the "Select Patient" button 92.

Figure 5:
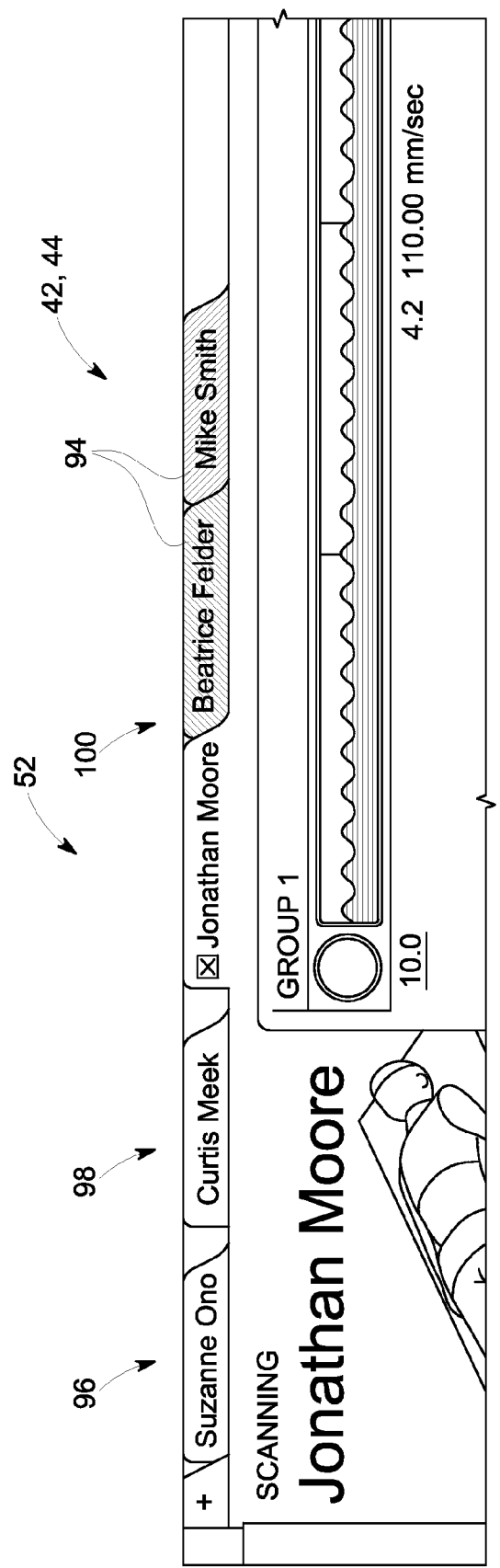
FIG. 5 is an illustration of a tabs zone on the dual display user interface of FIG. 3.

Referring now to FIG. 5, the tabs zone 52 is shown in greater detail. The tabs zone 52 in the user interface 42 introduces a flexible method of handling multiple patients (only one of which, however, can be "on the table" at any time), keeping patient information separate, and allowing a technologist to maintain control over what activities he or she would like to perform. Individual tabs 94 in the tabs zone 52 serve as a wrapper, containing both exam and patient specific information. The user interface architecture is designed to support multiple tabs 94, allowing a technologist to switch between exam activities, and supporting a multitasking workflow. Any selected tab 94 will span across both the left and right displays 44, 46. The structure of tabs zone 52 is highly efficient in handling patient surges or alternative scheduling methods, such as scanning patients back-to-back for long periods with the ability to easily return to post-processing at a later time.

Tabs 94 in the tabs zone 52 are ordered chronologically from left to right within the tabs zone. The tabs 94 appear starting at the top of the left display 44, with the most recently created tab 94 beginning on the far left-hand side. Within their chronological order, tabs 94 fall within three distinct clusters that communicate different phases of the workflow, including Not Yet Scanned 96, On the Table 98, and Done Scanning 100, with the clusters 96, 98, 100 being spatially separated from one another. The color of each tab 94 is also controlled to indicate the status of the exam it represents, with an exemplary color coding scheme being set forth below regarding various status indications while recognizing that other appropriate color coding schemes could also be implemented. For example, a white tab is a tab 94 currently selected and corresponds to the visible settings and viewports. This status shows which tab 94 a technologist is currently working within and is used in all tab clusters. There can only be one selected tab 94 at a time. When a tab 94 is selected, the white background replaces the current visual style (applies to all tabs). When the tab 94 is deselected (e.g., another tab 94 is selected), it is restored to the appropriate visual style. A gray background on a tab 94 communicates that there is nothing in the background being processed and that no particular action is required of the technologist. The gray background is considered a generic or neutral state and is used for all tabs 94 in the Not Yet Scanned cluster 96 and any tab 94 in the Done Scanning cluster 100 in which all required post-processing and data transfers have been completed. A tab 94 with a gray background and no name communicates that a tab 94 has been created but that the patient information and a protocol selection have not been completed, with such a tab status only being used only within the Not Yet Scanned cluster 96. A blue background on a tab 94 indicates the tab for the patient currently on the table, and thus this status is used only within the On the Table cluster 98. Since the currently selected tab 94 is always white, the blue background style is only seen when there is a tab 94 in the On the Table cluster 98, but a different tab 94 is selected. This is an additional method of communicating the uniqueness of this tab 94, along with the spatial separation of the On the Table cluster 98. The purpose of these unique visual differentiators is to reduce error and cognitive load when returning to the patient who is on the table. Gray diagonal lines on a tab communicate that image processing or file transfers are currently being performed and thus this status is used only within the Done Scanning cluster 100. Orange diagonal lines on a tab communicate that image processing is done, but that required Manual Reformats need a technologist's input and thus this status is used only within the Done Scanning cluster 100. A red background on a tab communicates that there has been an error that needs a technologist's acknowledgement or input, with the red color slowly pulsating to get a technologist's attention, but not be too distracting while they complete tasks in the currently selected tab. The red background status can potentially be used in any tab cluster.

Figure 6:
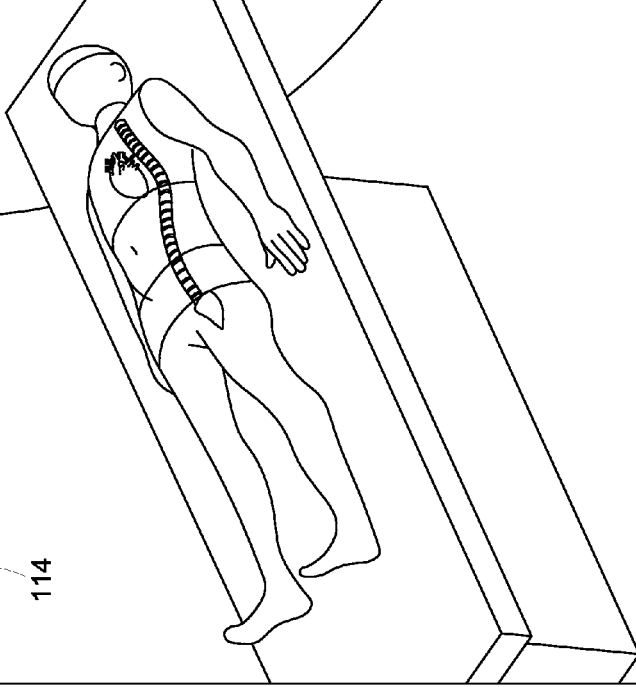
FIG. 6 is an illustration of an exam set-up and protocol zone on the dual display user interface of FIG. 3.

Referring now to FIG. 6, upon a command by the technician to create a new patient record or upon selection by the technician of an existing patient record that has not yet had information entered therein, either via the patient scheduler zone 50 or the tabs zone 52, an exam setup and protocol select area 102 is caused to appear related to the selected patient. The exam setup and protocol select area is presented on left display 44 and can extend down from a selected tab 94, for example, so as to be seen as corresponding to that tab 94. The exam setup and protocol select area 102 includes a patient information section 104 therein setting forth details regarding the specific patient, and also includes a plurality of protocol selection areas including: an anatomy selector/protocol filtering area 106, a protocol notes area 108, a protocol list area 110, a selected protocols area 112, and a smart type/find search area 114.

The anatomy selector/protocol filtering area 106 provides for selection of a particular portion of the anatomy that will be scanned by way of an illustrated anatomy present therein. The anatomy selector/protocol filtering area 106 also provides for selection of a particular protocol that will be followed for performing a scan on the patient, with a desired protocol being selected from a menu of favorite protocols and a menu of other protocols that are displayed therein, as well as being displayed in the protocol list area 110. Alternatively, a particular protocol can be selected by typing search term(s) into the smart type/find search area 114, with such a search having an auto-complete type feature (e.g., Google search) that provides possible suggested protocols to the technician. In evaluating protocols for selection, the technologist can reference the protocol notes area 108 to obtain more information on each particular protocol that is being evaluated.

As shown in FIG. 6, any protocols that are selected by the technician are shown in the selected protocols area 112 of the exam setup and protocol select area 102. The technician is thus able to review a list of all protocols that have been selected for performing on the patient and can click on an "Accept" button 116 in the selected protocols area 112 in order to confirm the selection of these protocols.

Any protocols that are selected and confirmed by a technician will appear in the patient area zone 54, which is shown in greater detail in FIG. 7. The patient area zone 54 encapsulates patient specific information at the exam level. The two main components within the patient area zone 54 are a patient illustration 118 and a patient collection 120. The patient/scanner illustration 118 in the upper left corner of the patient area zone 54 communicates six distinct pieces of information: Patient Name, Patient ID, Exam Number, Patient Position and Orientation, Anatomy selection (based on protocol(s)), and Gantry Orientation. The patient name is shown in the top right corner underneath the "SCANNING" label.

When a technician working on the user interface hovers the mouse cursor over the illustration 118, controls appear to indicate the possibility of changing the position and orientation of the patient. There are two possible gantry positions the illustration supports: facing away to the right and to the left. The appropriate orientation is set to reflect the actual physical orientation of the scanner. Having the orientation of the physical and the digital representation match should avoid any confusion when setting up the orientation of the patient. Areas of the anatomy covered by the selected protocols for the exam appear highlighted in the illustration 118, such as the Chest, Abdomen and Pelvis highlighted on patient illustration 118 in FIG. 7. These are the same highlighted areas that the technologist will see in the anatomy selector/protocol filtering area 106 of the exam setup and protocol select area 102 before creating the exam. A technologist should be able to clearly see if there is a part of the anatomy being scanned that should not be by examining the patient area zone 54.

The patient collection 120 contains settings for Landmark Reference, Patient Orientation, Patient Position, Auto-Voice Language, and Clinical Application Identifier. As shown in FIG. 7, the patient collection 120 is in an opened/expanded position so as to reveal the individual settings; however, the patient collection 120 can also be closed/collapsed to minimize the display of the collection.

Figure 8:
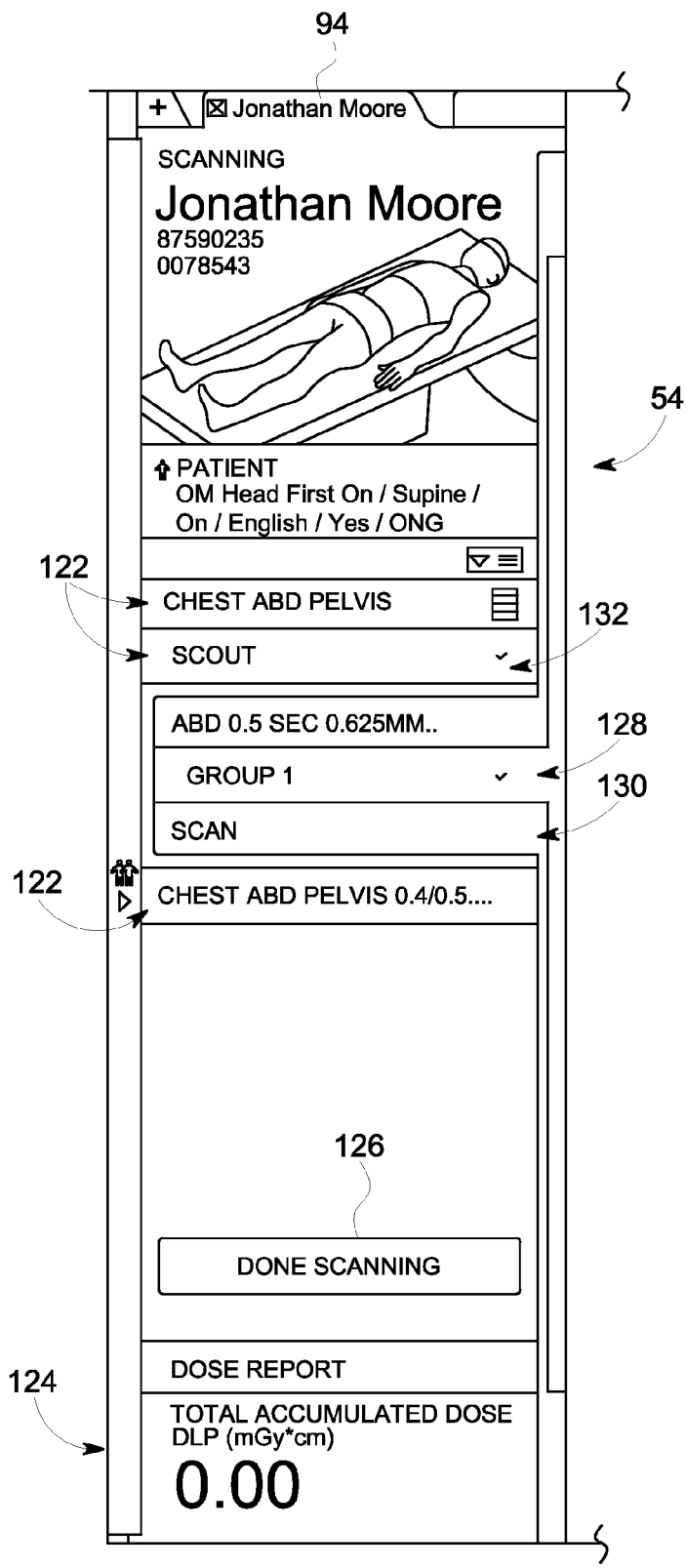
FIG. 8 is an illustration of a task zone on the dual display user interface of FIG. 3.

Appearing directly below the patient area zone 54 on the left display of the user interface 42 is the task list zone 56, which is illustrated in more detail in FIG. 8. The task list zone 56 of the user interface allows technologists to easily preview all steps prior to scanning. This visualization of all the steps in the scanning process gives technologists an opportunity to prepare, plan, and optimize the exam. This means that the technologist does not have to stop between each scan to adjust settings, allowing her to scan in quicker succession. The task list zone 56 helps guide the technologist through the process, increasing confidence, speed and patient safety.

At the highest level of the task list zone 56 are two main step or element types, in the form of Series steps 122 and a Dose Report step 124. Each of these main steps can contain sub-steps that will be visible when opened. Prior to and during the scanning of a patient, the Series steps 122 are visible in the task list zone 56, whereas the Dose Report step 124 is not present before or during scanning. In FIG. 8, as an example, three Series steps 122 are shown in the task list zone 56, with an opened Scout Series, an Abdomen (Abd) Series, and a Chest/Abd/Pelvis Series.

With respect to the Dose Report step 124, the Dose Report is the final step in the exam and is used to provide a dose summary. The Dose Report 124 appears once all prior Series steps 122 in the task list 56 have been completed or when a Continue and/or Done Scanning button 126 is pressed. If a step is added to the end of the task list 56 after the last step has already been completed, then the Dose Report 124 disappears until the newly added step has been completed or removed. The Dose Report 124 is displayed prominently and in large text in the task list zone 56 in order to facilitate reading this report at a distance, such as by technologists entering Dose Report information into another system across the room from the console.

With respect to the Series steps 122, a Series is defined as a collection of settings that are scanned together. Each Series step 122 is displayed in the task list zone 56, with each Series step including at least one Group sub-step (at minimum) 128 and one Scan sub-step 130. Each Series 122 has the potential to consist of a plurality of Groups 128 and a Scan step, with a Contrast step (not shown) also being included as required by the particular scan type. Each Group sub-step 128 is a collection of settings that is conceptually the same. The Contrast step looks like a Group step and can be clicked at any time. There can only be one Contrast step within each Series and it will always be the last step before the Scan step. The Scan sub-step 130 is always present and is always the last sub-step within a Series 122. To proceed to the Scan sub-step 130, all Group sub-steps 128 and the Contrast step (if present) must be confirmed. At that point, the system will automatically proceed to the Scan sub-step 130.

Each Series 122 can be displayed in one of a number of states to indicate to a technician the present state of that Series. The number of states includes: Not Yet Scanned, Open, Confirmed, and Completed. When a Series 122 is in an Open state, the Group sub-steps 128 and the Scan sub-step 130 are displayed. Each Series 122, and the Group sub-steps 128 included therein, can be placed into a Confirmed state via an affirmative confirmation by the technician that the steps are ready to perform. Indication of such a Confirmed state can be by way of a checkmark 132 placed to the right of the Series and/or Group sub-steps. Upon completion of a Series 122, the Series can then be marked complete to indicate that the Series is finished.

Figure 9:
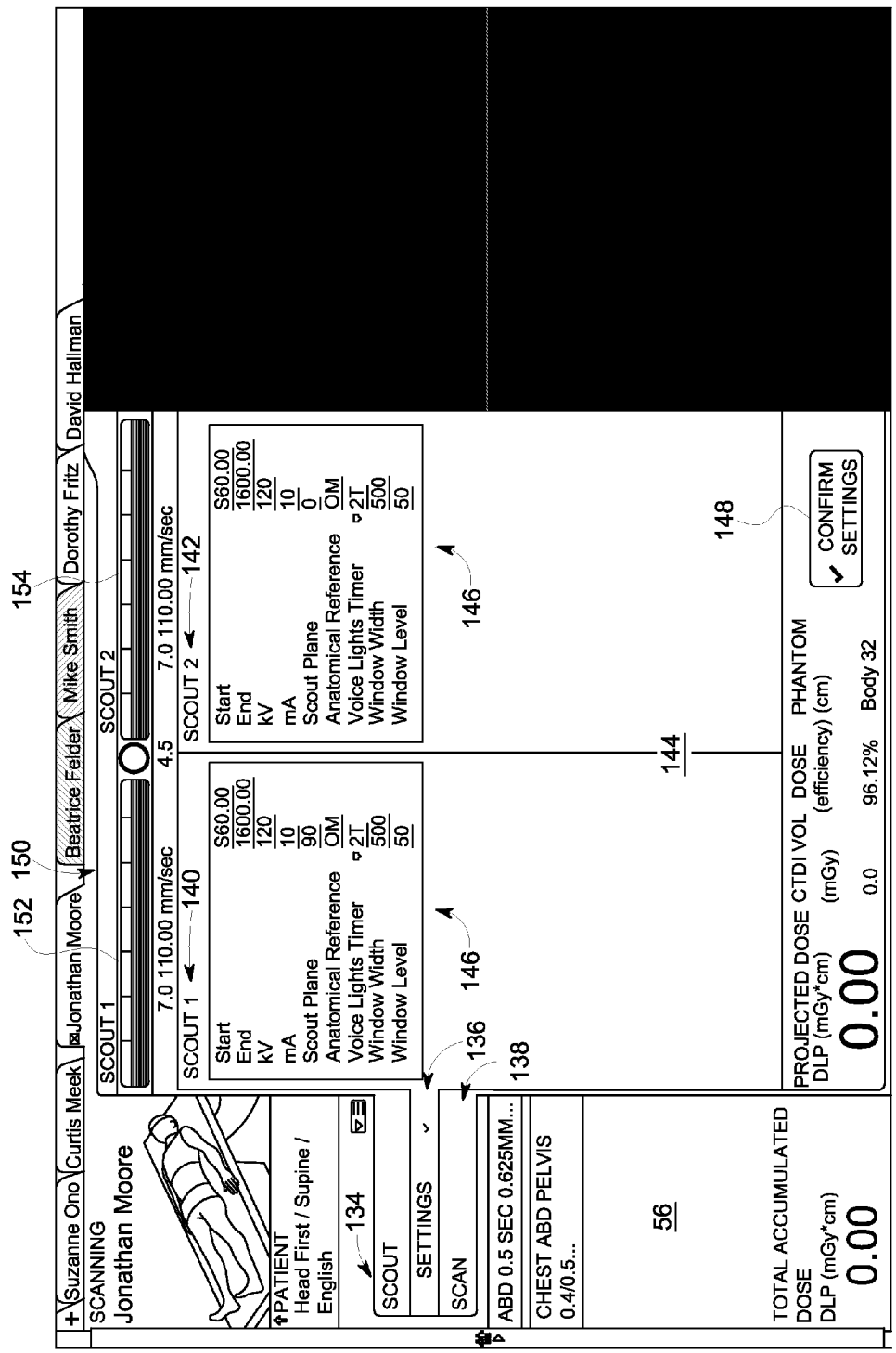
FIGS. 9 and 10 are illustrations of a scout zone on the dual display user interface of FIG. 3.
Figure 10:
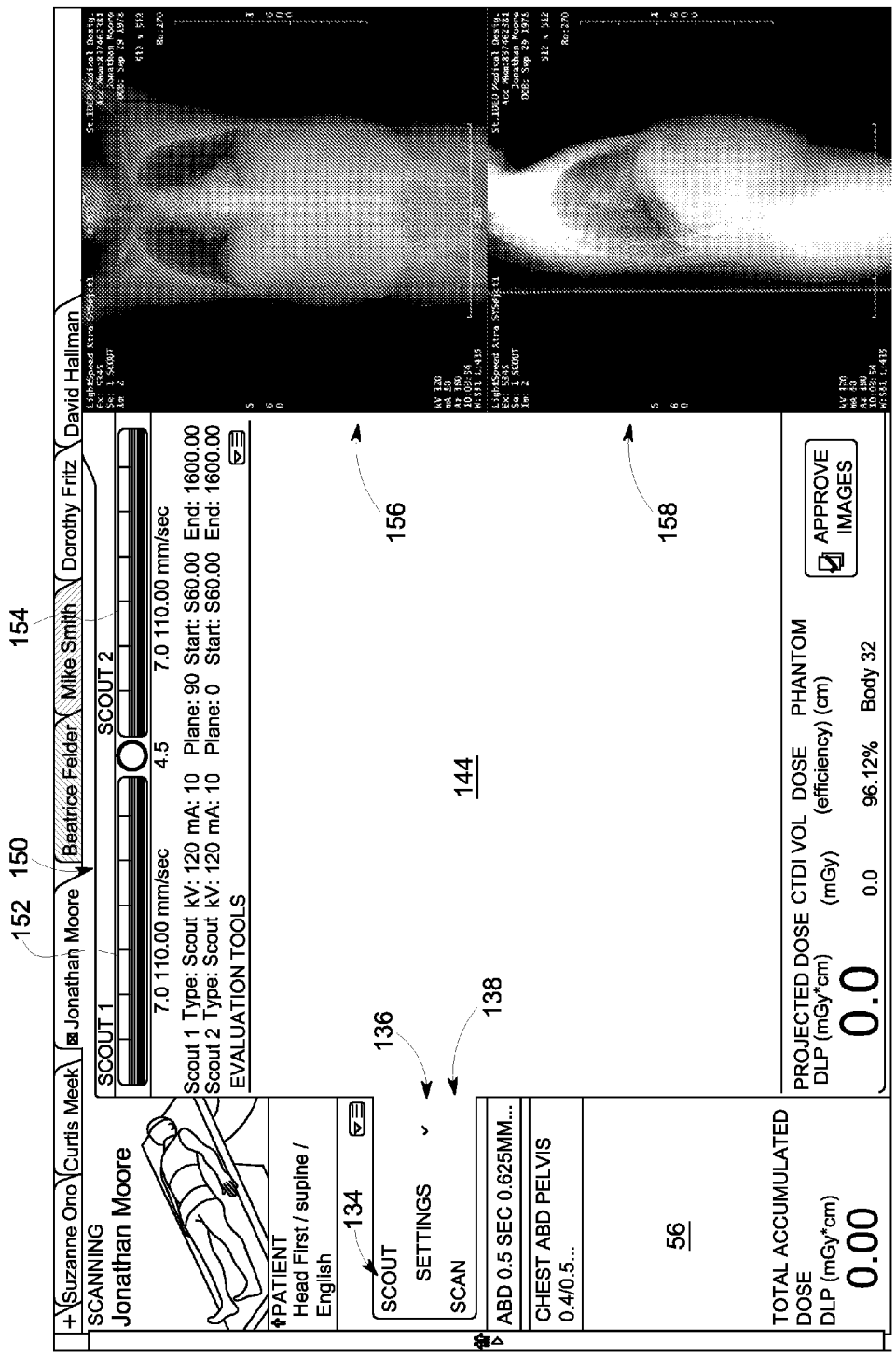

Referring to FIGS. 9 and 10, an exemplary Scout Series step 134 is shown according to an embodiment of the invention. As its name suggests, a Scout Series 134 is used to acquire Scout images. A Scout Series 134 always contains a Settings sub-step 136 as well as a Scan sub-step 138. The task list zone 56 can contain multiple Scout steps, which can be placed anywhere in the list of Series steps to be performed. For example, if there are two Scout steps, a technologist has the flexibility to either acquire both dual Scouts upfront or one dual Scout before the first Series step (e.g., Abdomen Series) and the second dual Scout before the second Series step (e.g., Chest/Abd/Pelvis Series). All Scout steps associated with all chosen protocols will be added to the task list zone 56. Additional Scout steps can be added or removed as desired.

In the example illustrated in FIGS. 9 and 10, two Scout Groups are included within the Scout Series 134, Scout 1 (A/P) 140 and Scout 2 (Lateral) 142. As shown in FIG. 9, when the Settings sub-step 136 is selected by the technician, the task list zone 56 is expanded to reveal a scout zone 144 that enables the prescribing of the two Scout scans 140, 142. In the scout zone 144, all Scout settings for each Group 140, 142 are displayed in the open settings collection state aligned beneath the Group title at the top of each of a pair of settings columns 146. A settings column 146 is presented for each Scout scan to allow the technician to individually change any unlocked settings in a Scout Group 140, 142 or make a global change to all Groups. A "Confirm Settings" button 148 is provided in scout zone 144 below the settings columns 146. Settings for both Scout Scan Groups 140, 142 are approved by clicking on the "Confirm Settings" button 148.

Also included in the scout zone 144 is a timeline 150 for the Scout series acquisition, with the timeline 150 consisting of a number of scan sections 152, 154 that are equal to the number of scout scan groups 140, 142. A Scout scan is represented within the timeline 150 as thin constant bars running the entire length of the timeline. According to one embodiment, if the two Scout steps 140, 142 in the Scout series 134 are being performed back-to-back, a delay is automatically created and inserted between the two scan sections allowing enough time for the table to return to its original position to acquire the second Scout scan.

Referring now to FIG. 10, upon clicking on the "Confirm Settings" button 148 (FIG. 9), the user interface 142 then proceeds to the Scan sub-step 138 of the Scout Series 134 for performing of the Scout series scans. When the two scout scans 140, 142 are acquired, viewports 156, 158 (in viewport zone 62, as shown in FIG. 3) on the left display 44 are used to display both scouts simultaneously, with the first scout scan 140 being shown in the top viewport 156 and the second scout scan 142 being shown in the bottom viewport 158.

Figure 11:
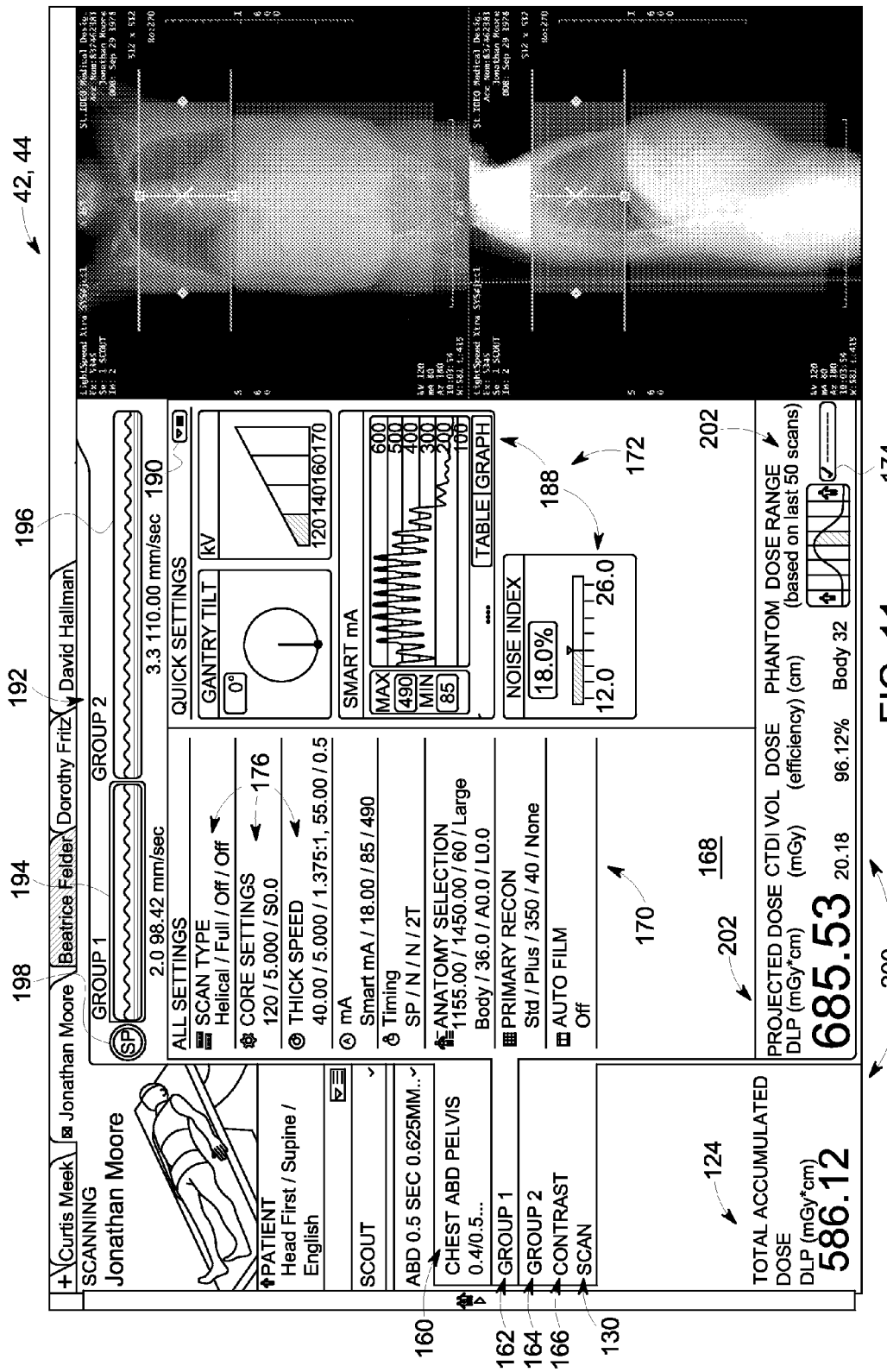
FIG. 11 is an illustration of a settings zone and a dose area zone on the dual display user interface of FIG. 3.

When the Scout Series has been scanned and the acquired image set has been approved, the system automatically opens the next Series in the Task List 56. Referring to FIG. 11, as an example, a Chest/Abd/Pelvis Series 160 is opened, with two Group sub-steps 162, 164 and a Contrast step 166 included therein for completion. As shown in FIG. 11, when a Group sub-step 162, 164 in the Series 162 is open, a settings zone 168 corresponding to that Group sub-step is displayed. The settings zone 168 enables reviewing of all settings at a glance with minimal interaction, so as to allow the actions of technologists to be directed and goal-driven rather than requiring them to do a lot of clicking just to double-check that everything is okay. The settings are divided into two areas, including a list view 170 of all settings on the left and a configurable and context relevant visual widget area 172, i.e., a "Quick Setting" area, on the right. Each of these supports the initial need to quickly review all settings defined in the Series protocol. Upon determining that action needs to be taken, the technologist can engage by either opening a settings collection from list view 170 or manipulating a widget from Quick Settings area 172, at which point the design focus shifts to allowing for clear, meaningful action that visually records the changes made in both an absolute sense and in relative relationship to dose. As seen in FIG. 11, the settings zone 168 is organized in logical collections containing three or more settings in each, with each collection being separated with a horizontal line. The settings are always in a set order and cannot be reorganized, so as to promote consistency and minimize confusion that could be caused by variable configurations. A "Confirm Settings" button 174 is provided at the bottom of the settings zone 168 to confirm the settings for a Group sub-step scan.

As shown in FIG. 11, the all settings list view 170 includes all settings that are available and relevant for the particular scan being performed. The nature of certain settings will dictate which collections and settings are available, with only applicable collections and settings being visible. Thus, as shown in FIG. 11, only settings relevant to a Chest/Abd/Pelvis Series scan are displayed. With respect to the relevant settings for the particular scan being performed, the setting are provided as settings collections 176 that are included in the all setting list 170, with each collection of settings 176 being in a closed state or an open state. As illustrated in FIG. 11, each closed collection 176 consists of a title with a unique icon to the left that represents the identity of the collection. In this state, some or all values of the parameters are viewable beneath the collection title in a single row. These values are separated by a forward slash, with the values using a different color. The rationale behind this closed state design (not keeping all the collections open all the time) is that it considerably minimizes the amount of perceived clutter of the user interface while still keeping all the settings in view, without requiring the technologist to scroll to see them. This gives the technologist instant visual access to the relevant information, albeit abbreviated. Although it might initially appear that just having the values without their respective labels at a glance is confusing, the consistent organization of the values, i.e., collection the value belongs to, position of the value in the row (whether it the first one in this collection or the third one) and the nature of the value (40.0 vs 500 vs 0.35 vs Full), allows for easy interpretation and familiarity over time.

Figure 12:
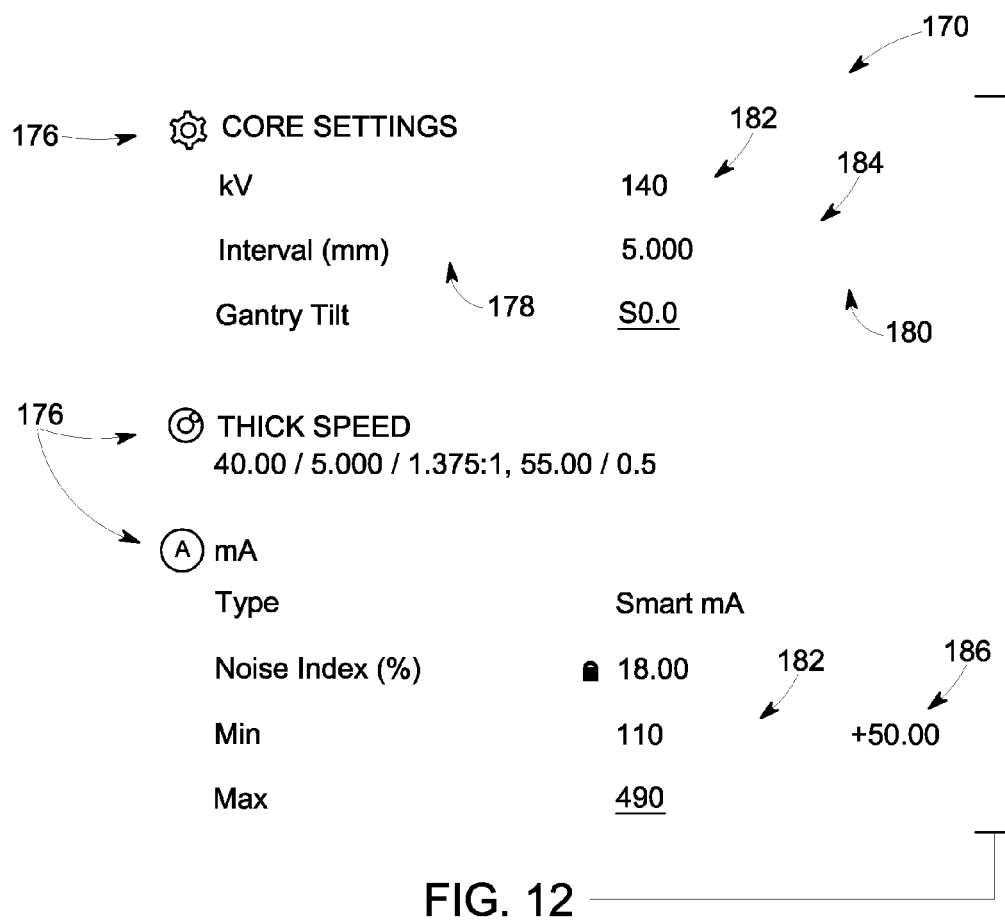
FIG. 12 is a detailed view of the settings zone of FIG. 11.

If more details are required, each collection of settings 176 can be changed from the closed state to the open state by way of a single click away, so as to expand the closed collection and reveal the details for all the settings in that collection. An example of a collection of settings 176 in an open state is illustrated in FIG. 12, where the Core Settings and mA collections are open. In the open state, the collection title and the icon remain visible and in the same position as the closed state and the settings are organized within the "frame" in a two-column vertical list. The left column 178 provides the titles of the settings, and the right column 180 contains the values. The setting value is underlined if it can be altered by the technologist. If the value is locked, there is no underline and a small lock icon signals that the technologist is not able to change the setting. Even though the setting is locked, it is displayed so that it can be reviewed. This allows the technologist to double-check the setting, offering a degree of validation and confidence to move forward. If the technologist questions the value, she can contact a lead technologist or radiologist (i.e., colleague with authority to approve and/or modify this setting) before initiating the scan.

With respect to the underlined settings that can be altered by a technologist, a color coding scheme is applied to identify setting values that have been changed (either directly or indirectly) and other setting values that might need attention based on any such changes. For example, if a value is changed by the technologist, the setting name and its value displays a white background highlight 182. The white change indicator allows for quickly discerning which settings have been altered from the original protocol. This "at a glance" means of communicating that a value has changed also makes it easier for collaborating technologists to determine whether a colleague made a change to the protocol while the other was performing another task (e.g., stepping away from the console to help the patient). Additional changes to setting values made by the system, in response to a user change, will briefly pulse white three times and also be colored white. A value changed directly by the technician will have both the white background 182 and the input method 184 visible, while a value that was indirectly changed will only have the white background. The combination of the change indicator and the "click-to-edit" will reveal which of the changes were made directly or indirectly by the technologist. If a value has been changed, and hence has a white highlight, and is then changed back to its original value defined in the protocol, the white highlight will disappear. In addition to the highlighting in white of a setting value that has been changed, changes that need attention (e.g., a clipped rotation in a modulated mA scan) will be colored orange and the Confirm Settings button 174 (FIG. 11) will still be active or available. Also, changes initiated by the user, that are not allowed and result in one or multiple system settings changes that need user attention, will be colored orange, with the Confirm Settings button then being grayed out.

Referring still to FIG. 12, if changing a setting impacts the predicted dose, the effect on dose (+/−DLP) temporarily appears in line with the value as a dose impact indicator (DII) 186, giving the technologist instant feedback. If the change is positive (increase in dose), a plus sign ("+") precedes the DII number 186 and the surrounding background is yellow. If the change is negative (less dose), a minus sign ("−") precedes the number and the surrounding background is a more neutral hue. The DII 186 will remain visible until a change to a different setting has been made. The number shown is always relative to the current projected dose, which means that changing a value such as kV "120" to kV "140", will not always result in the same DII value depending on the sequence of events. For example, imagine the projected dose is 1000 DLP and the technologist increases kV from "120" to "140". The DII 186 will display a change, say "+n %", and the impact its change had on the overall projected dose is now 1150 DLP.

Referring back now to FIG. 11, it is seen that the Quick Settings area 172 contains an assortment of visual settings widgets 188. These widgets 188 serve as an alternative to changing settings via the All Settings list 170 and represent either a single setting or a combination of settings based upon their design. If a change to a setting's value is made using a widget 188 it is reflected in the All Settings list 170 (e.g., such as the mA change shown in FIG. 12) and vice versa. The currently supported quick setting widgets 188 include: kV, Manual mA, AutomA/SmartmA or modulated mA, and Biopsy. The Quick Settings Area 172 is designed to be flexible enough to support current and future visual settings widgets. The widgets 188 shown in this area can vary between different protocols and across tasks within the left display (scan) task list 56. The lead technologist or radiologist can determine the preset group of visible widgets 188 appropriate for each protocol. This preset group can provide guidance as to what settings are "key" to the specific protocol and are more likely to need adjusting. The operating technologist can then choose to show or hide these and additional widgets 188 via the context menu 190 in the upper right corner.

When reviewing or changing settings in settings zone 168, a Scan Timeline 192 is always visible above the settings zone on the left display 44, as shown in FIG. 11. The Scan Timeline 192 also remains present during the Scan sub-step 130. The Scan Timeline 192 first appears after the Confirm Settings button 174 has been selected and prior to starting of the scan. The critical parameters associated with the scan type about to be scanned will displayed to the technologist, just beneath the Scan Timeline 192, supporting a final quality process check before irradiating x-ray. The Scan Timeline 192 represents all groups within the currently selected series (e.g., Chest/Abd/Pelvis) and has a background highlight indicating which particular group is selected. The Scan Timeline 192 indicates the overall time required to complete a scan for a particular Group, as well as the speed at which the scan will occur. According to an embodiment of the invention, the Scan Timeline 192 has three different visual treatments depending on the type of scan being run: Axial, CINE, Helical, Scout, or SmartPrep Monitor. If a single Series includes Groups with different scan types, then each respective segment 194, 196 of the Scan Timeline 192 will visually reflect the appropriate scan type for that Group. Each Group may have a delay before beginning the scan, with the delays being represented on the Scan Timeline 192 in the form of a delay indicator 198 that is in the form of a blue circle. The size of the delay indicator 198 is always consistent, regardless of the amount of time represented. Choosing a consistent shape/size for the delay regardless of time helps to emphasize the areas of the scan timeline 192 delivering dose. If delays were represented in a linear fashion, both the delays and the scan segments would have to be scaled smaller to fit within the viewable area, making it very difficult or near impossible to effectively view.

As further shown in FIG. 11, when a Group sub-step 162, 164 in the Series 160 is open, a visually prominent, dedicated dose area zone 200 is displayed beneath the settings zone 168 so as to clearly indicate to the technologist the impact of the exam settings. Within this dose area zone 200, technologists confirm exam settings and can view a simple dose visualization, both of which are designed to help ensure that the technologists are making informed decisions regarding dose. The dose area zone 200 includes the "Total Accumulated Dose" 124 value at the bottom of task list zone 56, and displays the amount of radiation the patient has already received during the course of the exam. This number increases to reflect every scan performed on the patient. The total dose amount 124 is associated with the entire exam versus only a particular Series or Group. Therefore, it resides below the Task List 56 as a summary for the entire exam. Also included in the dose area zone 200 is a "Projected Dose" 202 that displays a projected summary of the dose for a particular Group. This value is visible while the technologist is viewing settings for a Group 162, 164 and updates immediately as changes to settings are being made within the Group.

As further shown in FIG. 11, a dose range indicator (DRI) 204 is also included in the dose area zone 200 and is a visual representation of dose that provides the technologist with a reference point to help base his/her decision for what is an acceptable dose. It is understood that a varying degree of radiation is necessary for different body types, in order to produce images that are high enough in quality for diagnosis. The DRI illustration 204 helps the technologist perform a "sanity check" on the dose amount by factoring in these different body types. The DRI 204 compares historic dose information with the current projected dose 202 for a specific protocol (it should be displayed within all Groups for the protocol, but not in the scan step since multiple Groups might be scanned, at which point the DRI is no longer useful). The DRI 204 indicates where the projected dose 202 for the particular protocol falls within a normal distribution curve, making it clear to the technologist how, and to what degree, the scan deviates from or falls within the average. The goal of the DRI 204 is to provide the technologist with greater awareness and control of an acceptable dose amount without having them rely upon the overall maximum recommended dose value (which might be much higher than necessary).

Figure 13:
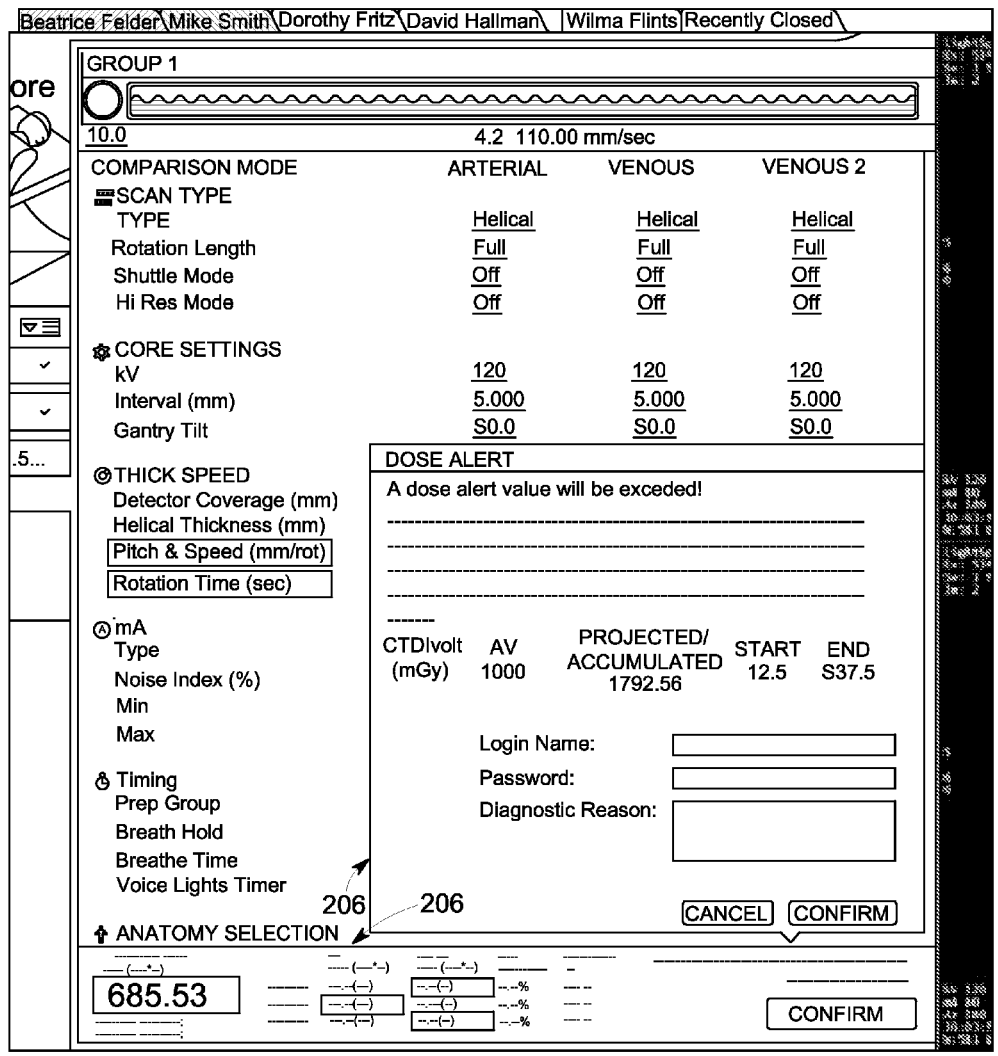
FIG. 13 is an illustration of an alert on the dose area zone of FIG. 11.

According to an exemplary embodiment, a dose check function is provided by the user interface 42 in the dose area zone 200. The dose check informs operators when scan settings would likely exceed pre-assigned dose thresholds (i.e., thresholds established by the healthcare provider based on their practice) and when the projected dose 202 for an exam exceeds the recommended maximum for a particular protocol. This allows technicians to confirm correct settings, prior to scanning, which might otherwise lead to unnecessary high levels of radiation exposure. The dose check function compares the estimated exposure from current scan settings to two different thresholds prior to scanning. Notification Values and Alert Values. The dose check function allows users to set a Notification Value that informs them when a scan prescription could deliver an x-ray dose over the Notification Value. The dose check function also allows users to set Alert Values that informs users when a scan prescription could deliver an x-ray dose that could result in deterministic effects. According to embodiments of the invention, alerts can be provided to the technician in the dose area zone 200 in some form. In one embodiment, and as shown in FIG. 13, a highlighted alert window 206 appears extending up from the dose area zone 200 that warns the technologist that the current dose settings have exceeded the recommended maximum for this scan. Confirm and Cancel buttons 208, 210 are presented in the alert window 206 that allow the technician to affirmatively confirm the settings or cancel out of the settings. According to additional embodiments, alerts can be provided to the technician in the form of the dose area zone 200 changing from blue to red or a disabling of the "Confirm Settings" button 174, making it very clear that this is a serious situation that needs to be carefully considered by the technologist.

Figure 14:
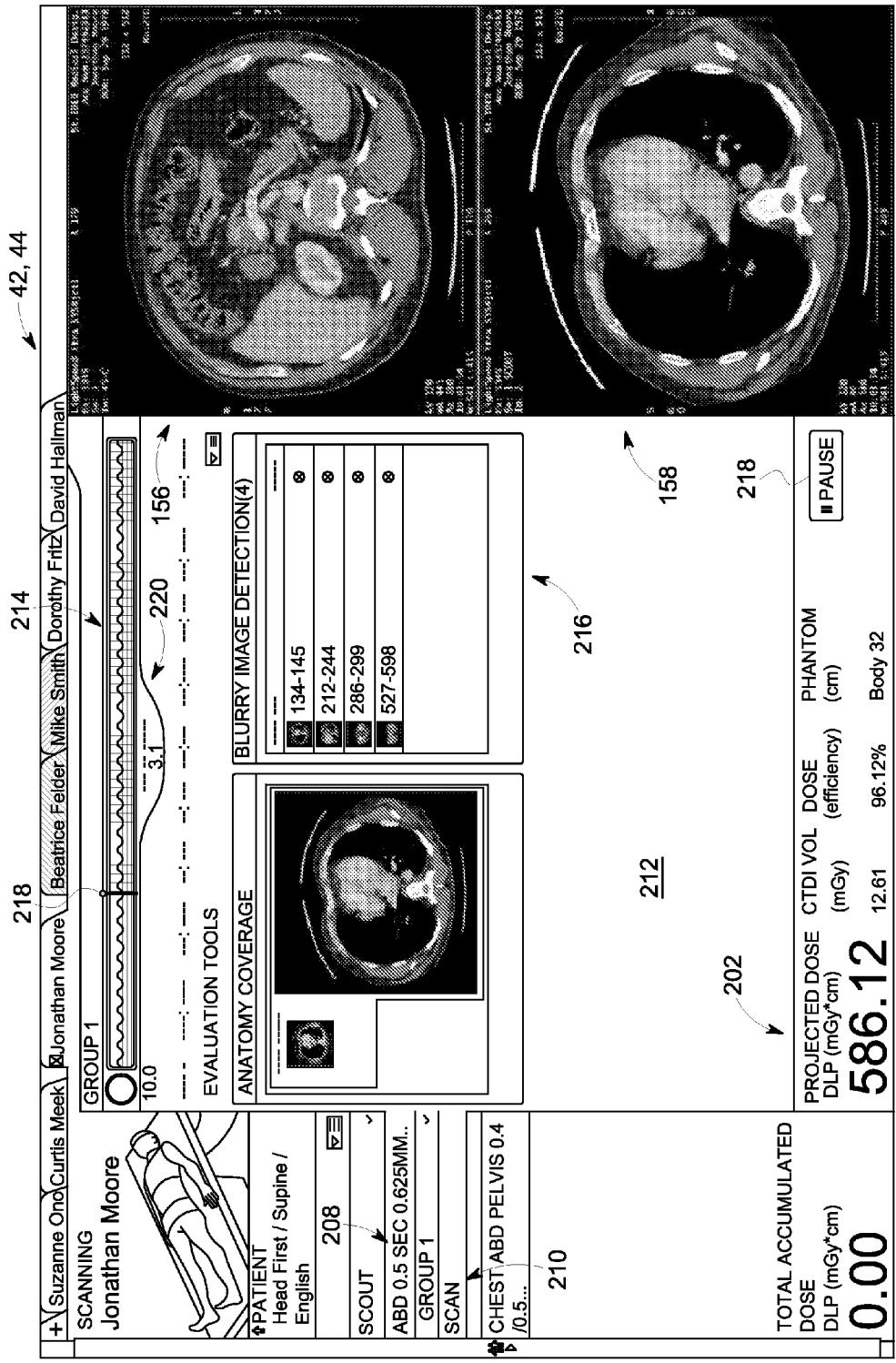
FIG. 14 is an illustration of a scanning zone and viewports zone on the dual display user interface of FIG. 3.

Upon confirming the settings for the Group sub-step(s) in a Series, the Scan sub-step of the Series is entered, such as for the Abdomen Series 208 illustrated in FIG. 14. When performing the Scan sub-step 210 for the Abdomen Series 208, the entire Series 210 in the Task List 56 visually connects to a scanning area/zone 212 to the right of the task list zone 56 by having the same background color thereas. When in the Scan sub-step 210, a Timeline 214 is presented in scanning zone 212 (i.e., a timeline for each Group in the Series), along with key settings 216 that can be further reviewed/revisited/changed, if desired. Also presented while in the Scan sub-step 210 are the Projected Dose 202 in the dose zone area 200 and viewports 156, 158 for displaying scan images.

The Scan Timeline 214 is a linear representation of the scanning segments within a Series and represents the state and behavior of each scanning segment (Group) along with additional steps based upon their particular types, including helical, axial, scout, delay scans, and Smart Prep (i.e., contrast), with each type being presented distinctively. Prior to scanning, all of the segments are represented along the timeline 214 but are visually "faded". Once the scanning process has begun, the Scan Timeline 214 becomes activated and provides a highlighted graphical progress indicator 218 of the scan. This highlighted marker 218 moves from left to right within the timeline 214, representing the particular point in the scan that is currently executing. As this highlighted marker 218 continues to move forward, the originally faded timeline area it passes "fills in" with a richer blue and brighter white color, for example.

The scan timeline 214 auto-scales in length proportionately to the total scan time, including any prep delays, to fit the area of the left monitor screen 44 allocated to it. When a section of the timeline 214 is completely filled in (be it a delay or a scan), the next section of the timeline automatically begins. If this automatic behavior is not desired, a technologist can create two separate Series in the Task List 56 instead of using two Groups. Under the timeline 214, a time (and speed) indicator 220 is displayed in white communicating how much time the particular scan will take. This number 220 remains white until the scan begins. Then, once begun, the number 220 turns yellow and counts down to reflect the remaining time for this step. The timeline 214 includes subtle vertical lines marking every second, with a very long scan therefore having many lines, whereas a shorter scan will only display a few lines.

As shown in FIG. 14, the key settings 216 for each Group to be scanned are listed immediately below the Scan Timeline 214, as required by regulations, with the Projected Dose Area 202 located below the key settings 216. The viewports 156, 158 associated with the Scan sub-step 210 are positioned to the right of the Scan Timeline 214 and the key settings area 216. Two viewports 156, 158 are provided on the left display 44, with the viewports 156, 158 being dedicated to the scanning process. An Auto-Link Viewport 156 on the left display is responsible for displaying the primary recon or preview images being acquired in real-time, as each image is reconstructed. A Navigation Viewport 158 is also provided in which the user can page through any images in the primary recon of the scan that is currently being acquired or was just acquired. Images are added to the Navigation viewport 158 as soon as they are reconstructed, but the viewport never automatically pages to the new image. Clicking within the Navigation Viewport 158 will cause it to be "selected" and, once the viewport is selected, the technician can use the "Page Up" and "Page Down" keys to navigate through the images. The left display Navigation Viewport 158 will be automatically selected when a new scan begins, ensuring that the technologist can immediately navigate through the newly acquired image set without additional steps.

Prior to scanning, the Auto-Link and Navigation Viewports 156, 158 are populated with images associated with the Scout scans (i.e., Scout 1 and Scout 2, respectively). White semi-transparent rectangles on the Scout images mark the area that is about to be scanned (see FIG. 11). Also prior to scanning, the Dose Area 200 displays the total projected dose for the Series (all Groups) that will be administered if the scan button is pressed. When a Scan/Pause button 218 (appearing as "Scan" before the scan is initiated) is pressed, key settings 216 associated with a Group step currently being performed are temporarily highlighted and both viewports appear empty (or "blank") until the first Scan image is available, at which point the Auto-Link and Navigation Viewports 156, 158 are populated as the images are acquired, as shown in FIG. 14. In the Dose Area, the Scan/Pause button 218 is then caused to appear as "Pause" upon pressing of the scan button. After a scan has been completed, the images can be approved by the technologist, thereby causing the Task List 56 to move down to the next Series (if any) and kick-off the post-processing items for all Groups in the current Series for which the scan was just completed.

Figure 15:
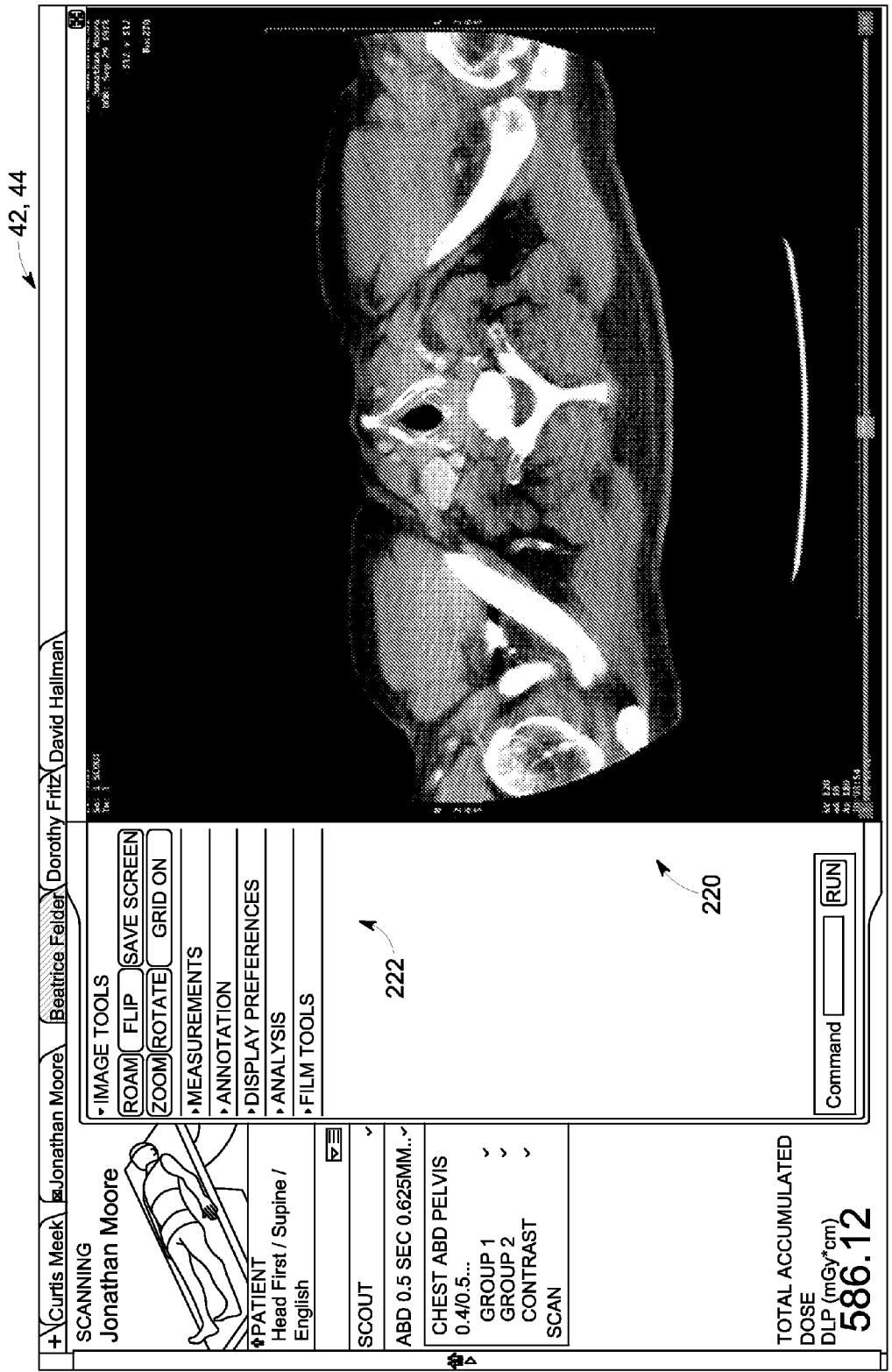
FIG. 15 is an illustration of an expanded viewport in the viewports zone of FIG. 14.

According to one embodiment of the invention, each of the AV and Navigation viewports 156, 158 on left display 44 can be expanded to a larger size, as shown in FIG. 15, by clicking an "expand" icon (not shown). The expanded viewport 220 appears on the same display as it's normal state, with the image presentation and the viewport remaining in the exact same state in the expanded size as in the normal size. The expanded viewport layout 220 contains a sidebar 222 with additional tools that allow the technologist to perform functions such as manipulating and annotating the image. The tools in sidebar 222 are organized in collections that can be opened or closed.

Figure 16:
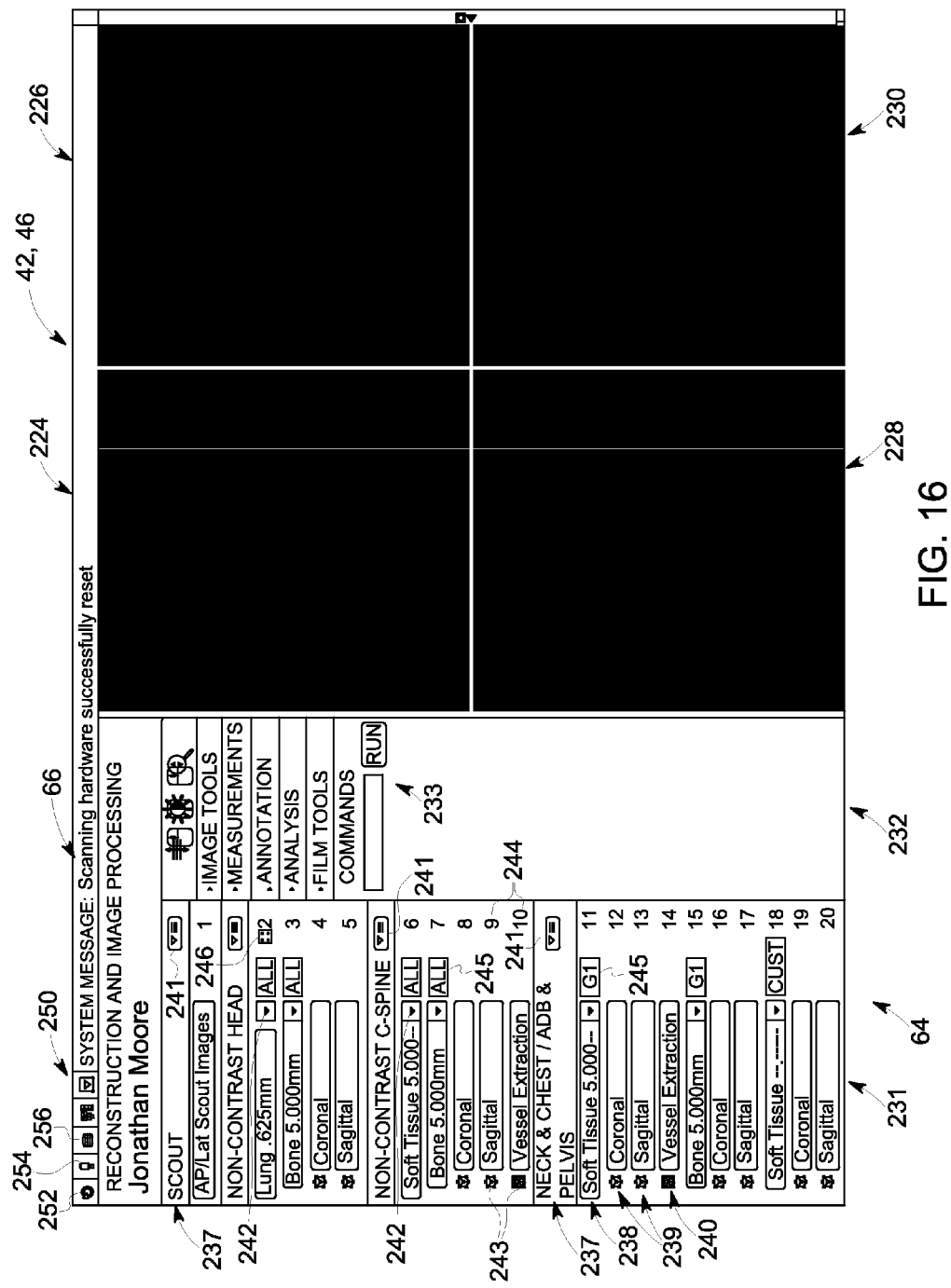
FIG. 16 is an illustration of a post-processing zone, status zone, and viewports zone on the dual display user interface of FIG. 3.

Referring now to FIG. 16, and with respect to the post-processing tasks initiated after completion of a scan, the CT user interface 42 utilizes the entire right display 46 for post-processing, creating the possibility for parallel workflows that avoid traditional bottlenecks. As shown in FIG. 16, a Post-Processing Panel or Zone 64 is provided on the right display 46 into which all post-processing tasks are consolidated, so as to provide the technologist with a quick overview of what post-processing is required for a protocol/exam and allow the technologist to manage all post-processing activities in one place, including: setup, monitoring, and transferring. Additional post-processing tasks during the scan process by way of the post-processing zone 64, including Recons and manual and automatic Reformats, with a technologist being able to choose to set up these tasks directly before scanning a series, set up all post-processing before doing any scans, or scan the patient first and then set up the post-processing.

Used in conjunction with the post-processing panel/zone 64 are viewports on the right display 46 are shown that are used in post-processing. As shown in FIG. 14, four viewports 224, 226, 228, 230 on the right display 46 are shown that are used in post-processing, including an Auto-Link Viewport 224 for displaying images that are rendered during the post-processing process and three Navigation Viewports 226, 228, 230 that allow the technologist to load and navigate through any finished Recon/Reformat image set from the post-processing list 64. The viewports 224, 226, 228, 230 on the right display 46 are spatially oriented and placed in context to what function they are serving.

According to an exemplary embodiment of the invention, any image set from a right display Navigation Viewport 224 can be loaded into a Floating Viewport (not shown). There is only one Floating Viewport displayed at a time, so loading additional image sets will add them to the Floating Viewport rather than create a new one. Image sets in the left head Navigation Viewport 156 (FIG. 14) cannot be loaded into a Floating Viewport because they have not yet been approved. The Floating Viewport is at a layer within the user interface that is higher than the tabs 94 in the tab zone 52 (FIG. 5) and is therefore not constrained to any particular tab and can be used to compare images across patients and exams. The Floating Viewport is thus designed to be moved and resized anywhere within the display area. However, as the Floating Viewport covers/obscures all other elements within the user interface 42, the Floating Viewport is constrained to the right display 46 only to prevent obscuring settings and other critical scan information on the left display 44.

Figure 17B:
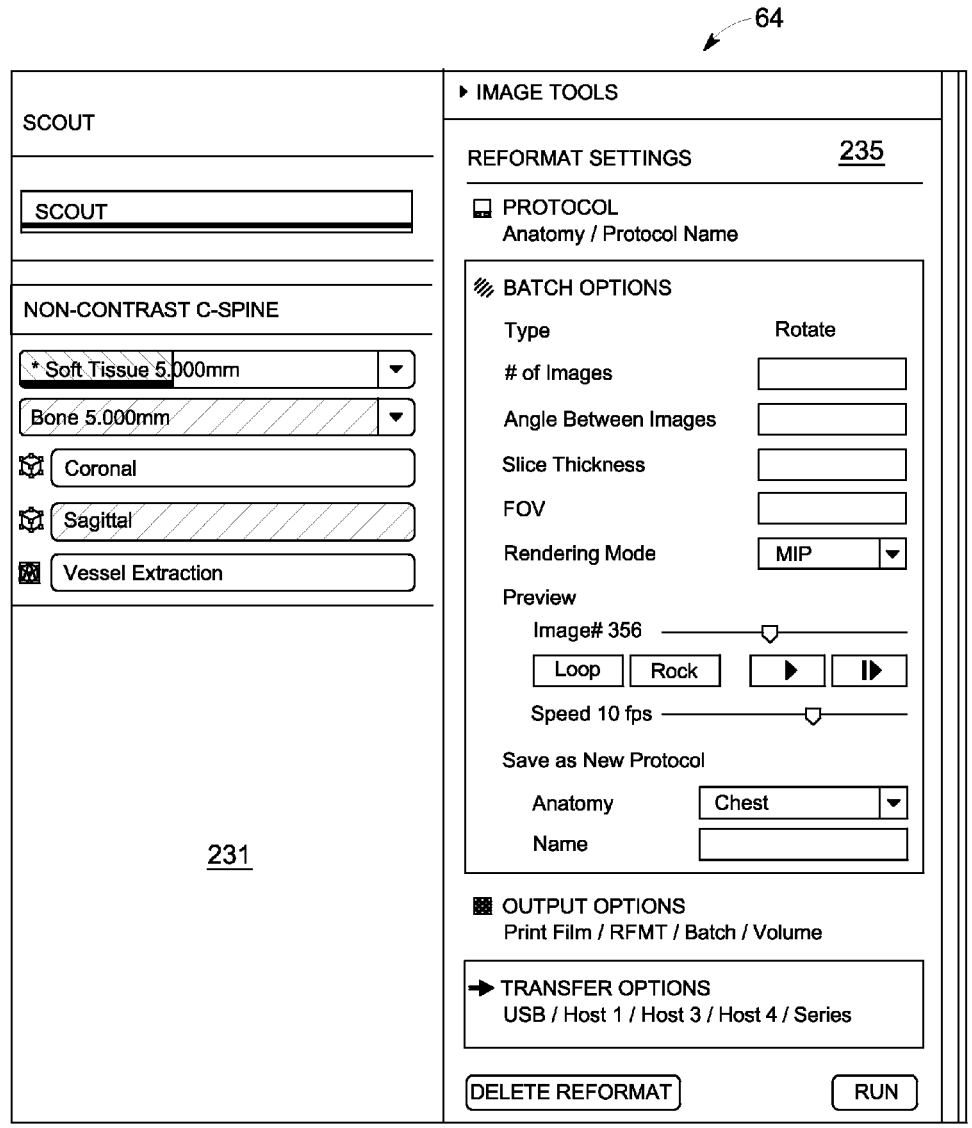
Figure 17C:
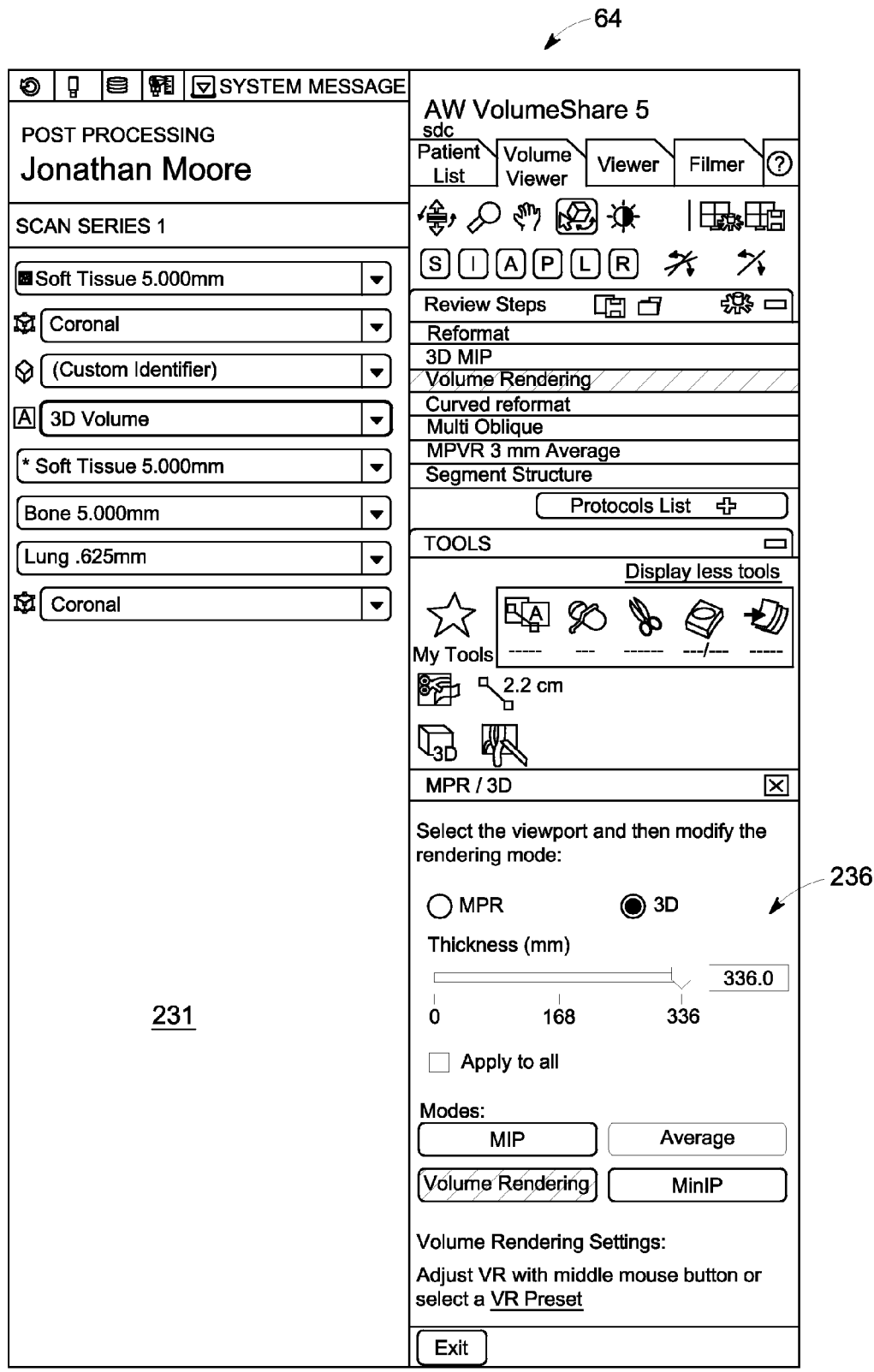

With respect to the processing and image display associated with post-processing, the Post-Processing Zone 64 on the right display 46 includes a Post-Processing Task List 231 forming a left column of the Post-Processing Zone 64 and a display tools area 232 forming a right column of the Post-Processing Zone 64, with a content of the display tools area 232 varying based on an operator's use of the of the Post-Processing Zone 64 and possibly displaying basic viewer tools 233 (as shown in FIG. 16, an Edit Settings Panel 234 (FIG. 17A), a DPMR application 235 (FIG. 17B), or an AW application 236 (FIG. 17C).

The Post-Processing Task List 231 allows a technologist to define transfer hosts for individual Recons and Reformats, AW advanced applications, as well as monitor both the creation and transfer of those image sets. As shown in FIG. 16, the task list 231 lists the Series 237 that are similarly defined in the Task List Zone 56 of the left display 44 (FIG. 8), and are named accordingly. Under each Post Processing scan series 237 are the Recons 238, Reformats 239, and AW task bars 240 that can be prescribed via protocol or before or after an exam. To the right of each series title is a context menu 241 that allows the technologist to create a new Recon at any time. According to embodiments of the invention, the context menu 241 may provide for Recon of the entire anatomy scanned within the scan series, Recon of a particular scan group within the scan series, or Recon of a unique area within all anatomy areas scanned.

In an exemplary embodiment, each Recon and Reformat task bar 238, 239 serves as both a process status indicator for the image set it is responsible for as well as a means to toggle the visibility of its settings. To edit a Recon, the technologist can click on a particular Recon task bar 238 and it will open the Edit Settings Panel 234 (FIG. 17A) in the display tools area 232 to the right of task list 231 to allow the technologist to make changes to the settings. For example, Recon Settings, Anatomy Selection, Cardiac (if applicable/available), Output Options, and Transfer Options, may all be edited in the edit settings panel 234. Each Recon task bar 238 also includes a drop down context menu 242 that allows the technologist to duplicate the current recon to create a new one, create a new Reformat based upon the Recon image data, and/or send the Recon image data to a specific AW tool to create a Reformat or perform any other relevant AW task. Similarly, to edit a Reformat, the technologist can click on a particular Reformat task bar 239 and it will open the DPMR application 235 (FIG. 17B) in display tools area 232, with the DPMR application providing for viewing of all reformats, editing the name of the reformat or any settings of any reformat, and editing transfer settings. The user can thus manually edit the Reformat as desired via the DPMR application 235.

To communicate the processing status of a Recon/Reformat, the status bars 238, 239, 240 are color coded to indicate the processing status. For example, the status bars 238, 239, 240 may be color coded such that White (solid) indicates that Processing has not started, Gray with diagonal hash marks indicates Current processing, Gray (solid) indicates completed processing, Orange hash marks (still) indicate that the MPR is ready to be defined (i.e., as soon as the Recon is done, the MPRs can be defined and started), and Gray with diagonal hash marks indicate that an MPR has been defined but has not yet started (still hash marks) and/or that the MPR has reached the top of the processing queue and that processing has begun (hash marks moving).

Also included in the post-processing task list 231 is a plurality of icons that provides more information on a specific Recon, Reformat, or AW task bar 238, 239, 240. One such icon is included in front of the control for each Reformat or AW task 239, 240, where there is an indicator 243 of the task type. These indicator icons 243 can communicate that the Reformat that has been defined, that the Reformat does not have a protocol and therefore requires the user to define its settings manually, or if a task is an AW task. To the far right of each Recon, Reformat, or AW task bar 238, 239, 240 is the series number 244 that will be or has been assigned to that image series. For multi-group acquisitions, an anatomy label 245 to the right of the Recon bar 238 indicates the part of the scanned anatomy the Recon is covering, such as an "ALL" label if the Recon start and end points correspond exactly with the entire scan acquisition or a "G1" label if the Recon start and end points correspond exactly with a single scan group. A viewport icon 246 is selectively displayed to the right of the anatomy label 245 as soon as any image exists for an image series, with the viewport icon indicating which viewport each image series is displayed in.

Referring again to FIG. 16, also included on right display is a status area zone 66 designed to communicate and enable several system states and functions of the CT scanner and console. It also allows for switching between separate Scanning, Protocol Management, and Service modes. All information within the status area zone 66 is exam independent, which is why it is separated spatially from the post-processing task bar 231 of Post-Processing Zone 64. As shown in FIG. 16, the status area zone 66 is located within the topmost bar of the right display 46. Icons 250 found in the status area zone 66 are designed using neutral shades of color for normal or expected operational conditions so as not to be intrusive. Color and additional text is reserved for when a technologist needs to take action. Drop-down menus are presented after clicking any icon, which allows for various actions to be taken. The Mode icon 252 is the first icon starting at the left-hand position within the status area. To change modes, a technologist can click the icon and a different mode can be selected from the drop-down menu, selecting from a scanning mode, protocol management mode, or service mode. This icon will change to reflect the current mode selected. The tube icon 254 provides information (e.g., tube temperature information) and functions in response to the current state of the scanner x-ray tube and is the second icon from the left. The available disk space icon 256 communicates the amount of available disk space on the system, with different warning levels being set by the lead technologist.

Figure 18:
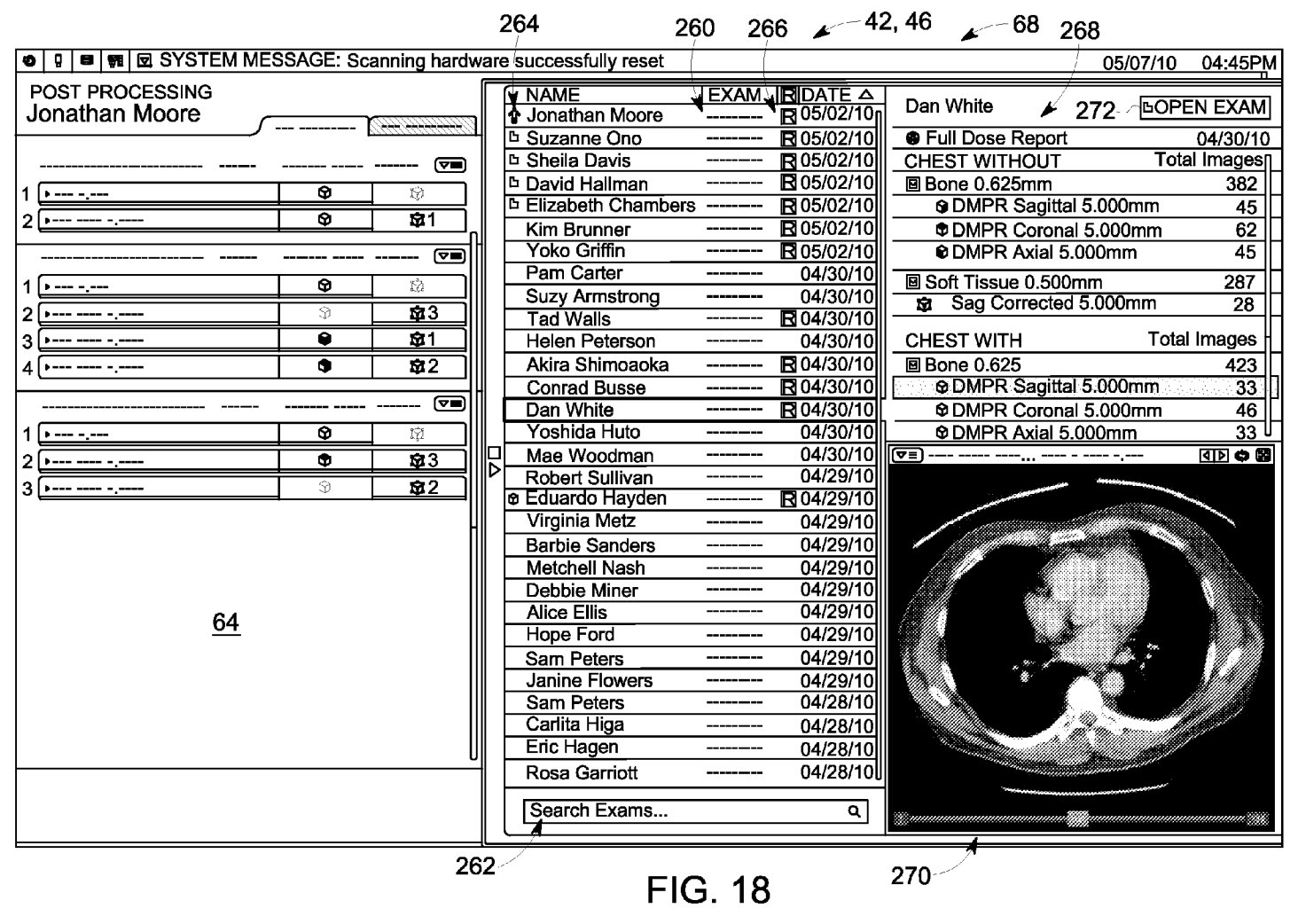

Referring now to FIG. 18, the file manager zone 68 included on the right display 46 is shown in an opened state. The file manager zone 68 is one of two "drawers" (the other is the Scheduler Zone 50) within the user interface 42 that are consistently present in either a closed or open state. The file manager zone 68 is located on and anchored to the right side of the right display 46. Because the file manager zone 68 is a feature associated with the console as a whole, and not a particular exam, it exists on a higher layer than any tabs that might be open. The rationale for this design is that it allows a technologist to access the file manager zone 68 at any point, quickly handling unexpected situations or pulling up past scans. Tasks enabled by the file manager zone 68 generally include setting up future and/or final steps in any workflow, thus it is found on the right side of the right display 46 in order to reinforce the left-to-right workflow concept embodied by the user interface 42 architecture.

The file manager zone 68 serves several main functions including: exam organization and status, access to files, opening an exam, quick viewing, and quick networking. On the left side of the open file manager zone 68 is the exam list 260, containing all current and previous exams that are still stored on the console. At least one of these exams is always selected (by default the latest exam). There are three sortable columns of information: Name, Exam, and Date. An exam appears in the exam list 260 once the first image is captured from the first step in the Task List 56 (FIG. 8). At the bottom of the list 260 is a search box 262 that can be used to find specific exams based upon keywords. There are also two icon columns that are used to inform the technologist about the state of the exam: Exam Status 264 and Data Status 266. There are three different types of icons that will appear within the Exam Status column 264 when applicable, including: Patient on Table, displays an icon of a person to the left of the patient name if the exam is open and that patient is currently on the table; Open Tab, displays a tab/folder icon to the left of the patient name if the exam tab is currently open, but the patient is not on the table; and Post-Processing Not Finished, displays an empty, dotted outline of a cube to the left of the patient name if the exam tab is not currently open and post-processing for the exam is not 100% complete (automatic or manual).

Selecting an exam from the Exam List 264 will open it in the Selected Exam area 268 on the right side of the File Manager zone 68. A Final Dose Report, List of Recons and Reformats, and all images associated with the exam are then available to be previewed. The Full Dose Report provides a complete summary of the dosage from the exam (similar to the dose report used in the traditional GE CT UI) and appears as the first list item in the Selected Exam area. The list of Recons and Reformats associated with the selected exam are organized in a similar manner to how they are structured within the Post-Processing Area. Each Recon in the list includes a Recon icon, the name of the Recon filter, the slice thickness and the total number of images. Slightly indented below a Recon are the associated Reformats. Each Reformat includes the type (e.g., "DMPR" or "Manual Reformat") and thickness, as well as the total number of images. Upon selecting any of the Recons or Reformats they will be previewed in the Image Preview viewport 270 located in the lower right side of the file manager zone 68.

The "Open Exam" button 272 found within the Selected Exam area 268 allows a technologist to reopen an exam tab 94, which will return that tab to the exact same state as when it was closed. Therefore, if an exam was aborted prior to completing post-processing, it can be reopened and a technologist can continue from where they left off. Additionally, a technologist or radiologist can review all of the steps, settings, and post-processing actions that were taken during the exam for quality assurance, research, or training purposes.

By way of the post-processing zone, status area zone, and file manager zone, the right display 46 thus provides a technologist with an organized and efficient mechanism for handling all post-processing tasks. By utilizing the entire right display for post-processing, the possibility for parallel workflows is created that avoid traditional bottlenecks. Additionally, by consolidating all the post-processing tasks into one area, this provides the technologist with a quick overview of what post-processing is required for a protocol/exam, with a technologist being able to manage all post-processing activities in one place, including: setup, monitoring, and transferring.

In addition to the above features found on user interface 42 set forth above, and the corresponding benefits provided by such features, it is recognized that the user interface is configured a flexible, extensible user interface that can be adapted to meet specific needs of a technologist. Set forth below are two examples of the ability of the user interface 42 to provide/meet the unique functionality or needs associated with particular scanning protocols.

Figure 19:
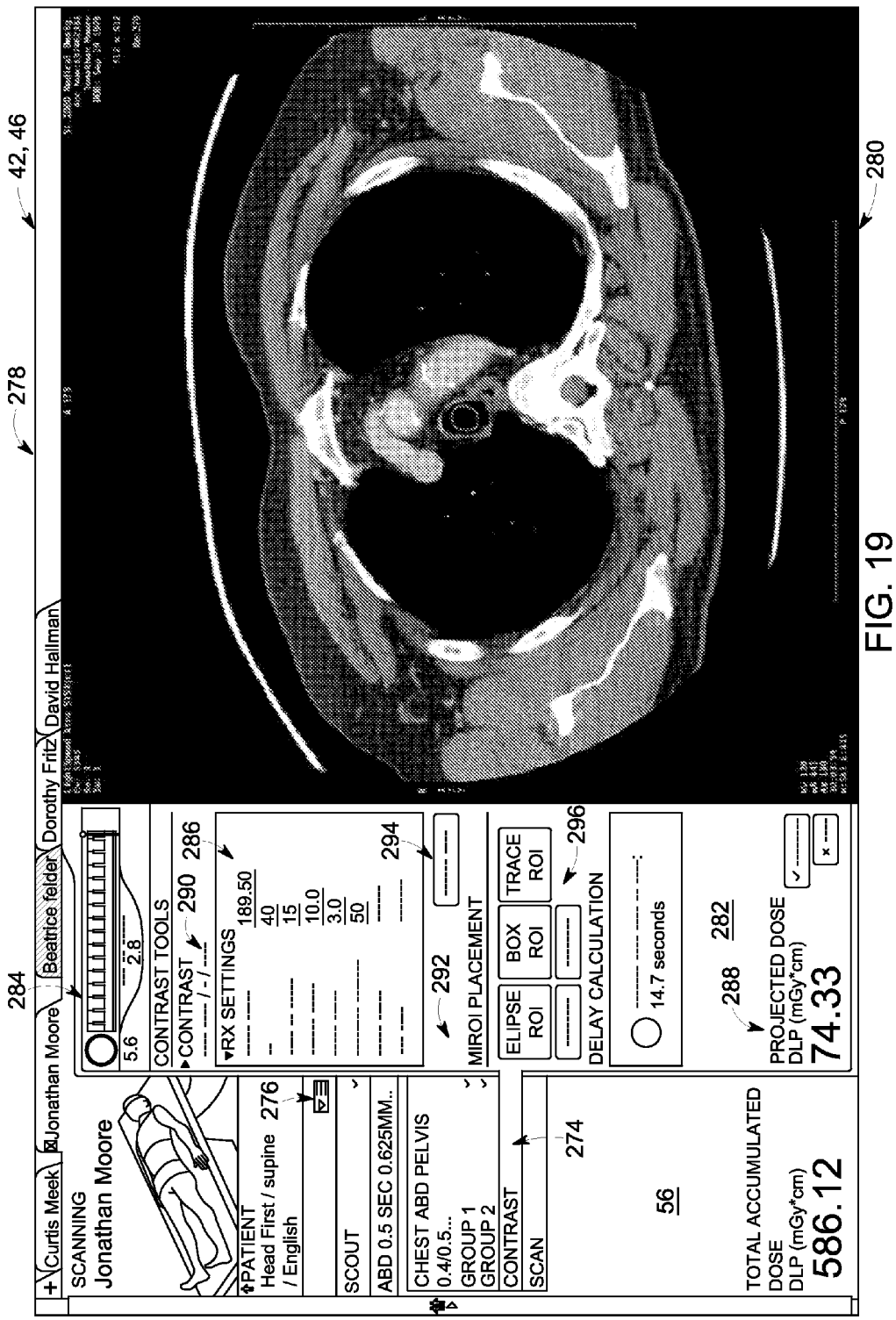
FIG. 19 is an illustration of a contrast monitoring zone on the dual display user interface of FIG. 3.

Referring to FIG. 19, as a first example, presentations provided by the left display for a contrast scan are provided. It is recognized that the standard of care for contrast enhanced CT studies is manual "Timing bolus" or a semi-automatic/dynamic contrast enhancement technique called "SmartPrep". Smart Prep and Timing bolus are two ways of determining the initial delay for a scan when using a contrast agent and, in essence, are tools for acquiring images to use for calculation instead of diagnosis. When performing a contrast scan, a Contrast sub-step 274 is added to a Series step in the Task List 56, regardless of whether it involves Smart Prep or Timing Bolus. If the Contrast sub-step 274 is not configured as part of the protocol, it can be added to any Series step via the context menu 276 in the upper right corner of the Task List 56.

A Contrast sub-step 274 works very much like any other sub-step, in that it can be viewed (selected) and confirmed at any time on left display 44. However, as shown in FIG. 19, the layout of a contrast zone 278 associated with the Contrast sub-step 274 is different from the layout for other Group sub-steps. That is, contrast zone 278 features a Double-Size Viewport 280 and a single, narrower, settings panel 282 on the left. This panel 282 includes a Scan Timeline 284 at the top, settings and tools 286, and a Dose Area 288 at the bottom. The specific content of the panel 282 is dictated by the value of the Type setting 290 within the Contrast Collection, i.e., "Smart Prep", "Timing Bolus", or "Unaided"—with FIG. 19 illustrating a Timing Bolus presentation, as an example. In use, an image acquisition from a contrast scan results in an initial axial image that is needed to place the ROI being loaded into the viewport 280. After an image has been acquired, a small thumbnail image 292 of the previously acquired Scout appears to the left of the "Acquire Image" button 294. This thumbnail 292 allows a technologist to toggle between the Scout and Contrast images. Once an image is acquired and visible in the viewport 280, ROI Placement tools 296 are enabled and can be used to specify the ROI. The settings listed in the collections will change to reflect the settings used when acquiring the image being viewed. The location in which the technologist places the ROI, and the settings associated with that image acquisition, will be used during the monitor phase in the Scan step when acquiring additional images.

Figure 20:
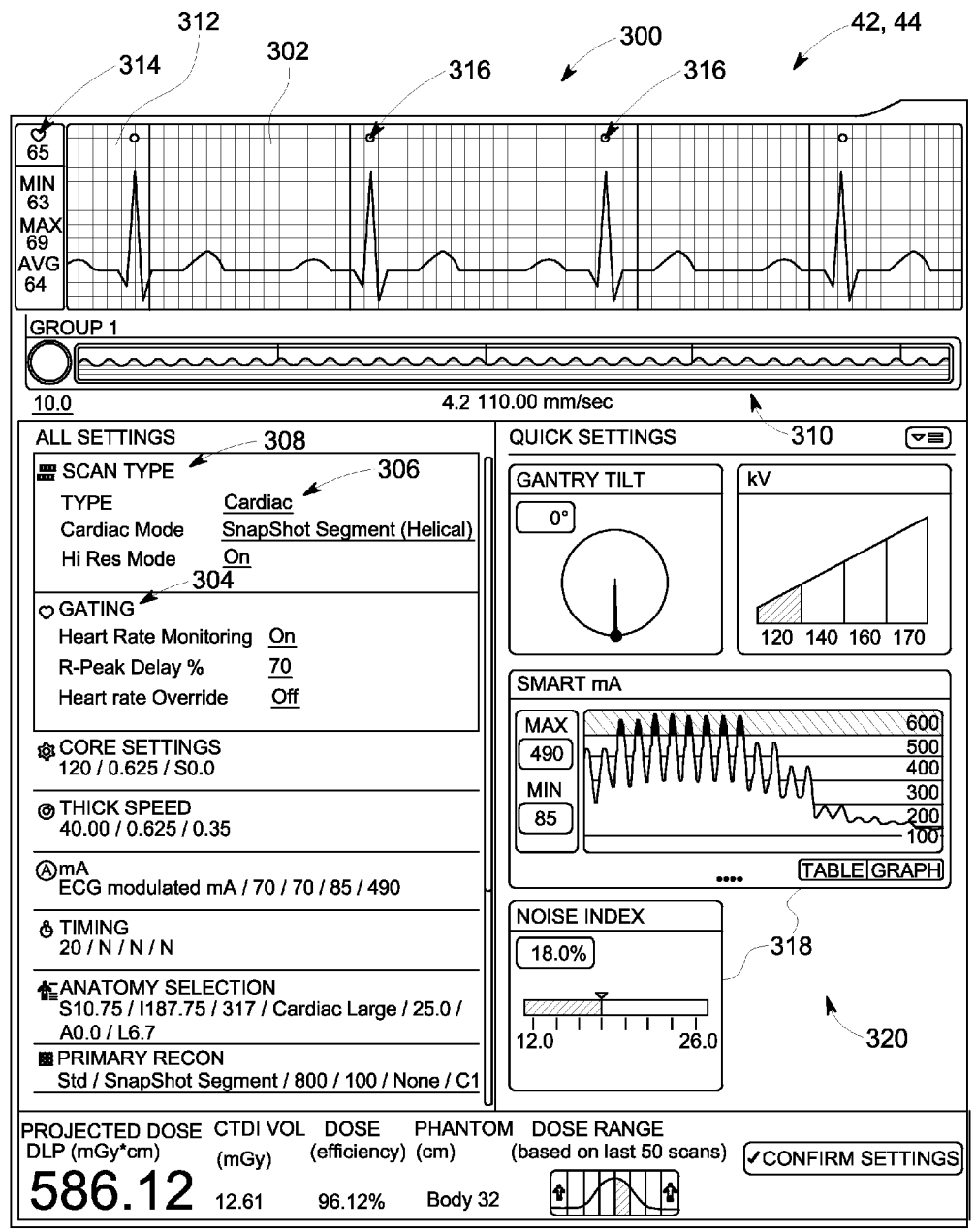
FIGS. 20 and 21 are illustrations of a cardiac zone on the dual display user interface of FIG. 3.
Figure 21:
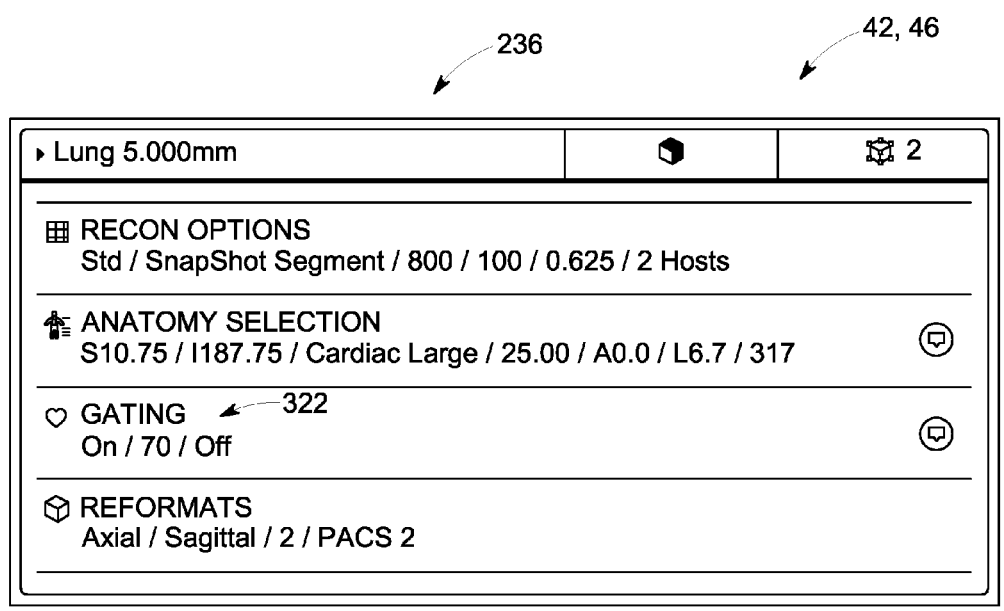

Referring now to FIGS. 20 and 21, as a second example, presentations provided by the left and right displays 44, 46 for a cardiac scan are provided. Performing a cardiac scan requires additional cardiac-specific user interface components and settings to be available to a technologist. As shown in FIG. 20, on the left display 44, these components/settings are provided in a cardiac zone 300 and include the ECG Monitor 302, Gating & Monitoring Collection 304, and individual settings within existing collections such as Cardiac Mode 306 within the Scan Type Collection 308. The ECG Monitor 203 appears at the top of the main area above the timeline 310 for use in cardiac scans. Above the R-to-R Interval value 312, a small heart icon 314 flashes to reflect the patient heartbeat (BPM). A small white dot 316 above each peak marks each R-to-R Interval visually on the ECG trace 302. The user interface architecture can also support potential cardiac-related widgets 318 in the Quick Settings area 320, to be added as necessary. As shown in FIG. 21, with respect to the right display, a Gating & Monitoring Collection 322 is added to the Recon Settings for cardiac scan types within the post-processing panel 236.

The availability of Contrast and Cardiac-specific components and settings is a strong example of how the user interface has been designed to have a flexible architecture. While these two specific examples of particular scanning protocols have been set forth above with respect to the flexibility/extensibility of the user interface 42 to provide/meet the unique functionality or needs associated with such protocols, it is recognized that additional components and settings can be added to the user interface to meet any type of scan types that may be developed going forward to meet the specific requirements of such protocols. In meeting the requirements of those protocols, the architecture of the user interface is such that the interface will maintain consistent patterns of behavior, while adapting to specific needs and reducing clutter when a component or setting is irrelevant.

Beneficially, embodiments of the invention thus provide a dual display CT user interface that offers technologists the confidence and functionality to complete scans more efficiently and to do so while improving quality assurance and better protecting patient health. The user interface design facilitates multitasking by breaking the trade-off between the number of parallel tasks performed and the likelihood of error and also facilitates improved radiation decision making by offering better visibility into dose and image quality trade-offs. The user interface design also provides radiologists with remote oversight capability and offer technologists flexibility to reduce process steps, including shortcut customization in places. The user interface design reduces the post-processing burden for technologists by automating tasks previously requiring manual attention and provides a framework to support an open protocol ecosystem that allows hospitals to share protocols and workflow best practices.

The dual display CT user interface also beneficially provides a workflow design framework that supports the steps/activities performed by the technologist associated with one or more scans. The left display is responsible for scanning—including setting up a new patient to scan and acquiring and verifying the scan image data—while the right display is responsible for post-processing—serving as a dashboard of Recons and Reformats that the technologist can glance through and verify what processes are configured, started, need attention, completed, or have been transferred. By organizing workflow activities within logical groupings on the left and right displays, technologists are able to focus on a particular task and multitasking constraints are alleviated. Clear, distinct identities for the displays containing the architecture are developed and incorporated into the user interface. As it is recognized that the scanning step demands the most focused attention from the technologist, the user interface displays are structured/laid-out to support this focused attention, providing only the necessary tools and views that the technologist needs in order to perform specific activities. That is, the user interface displays to a technician only those tools/settings that are required to perform a specific case, with a simple example being in cardiac CT, where context sensitive Cardiac user interface components are only provided during the Cardiac exam, and other, unnecessary general user interface elements retreat to the background so as to simplify the user interface.

Therefore, according to one embodiment of the invention, a user interface for a CT imaging system includes a first display configured to enable an operator to perform set-up and scanning tasks associated with performing a CT exam on one or more patients, with the set-up and scanning tasks including acquiring and verifying scan image data. The user interface also includes a second display configured to enable the operator to perform image post-processing tasks associated with the CT exams on the one or more patients, with the image post-processing tasks including performing image reconstructions and reformats. Each of the first display and the second display are operable independent from one another to provide for parallel workflows between the first display and second display and between the patient set-up and scanning tasks and the post-processing tasks.

According to another embodiment of the invention, a user interface for a CT imaging system includes a first display configured to enable an operator to perform set-up and scanning tasks associated with performing a CT exam on one or more patients and a second display configured to enable the operator to perform image post-processing tasks associated with the CT exams on the one or more patients. Each of the first display and the second display are configured to display a plurality of distinct display zones thereon, with the plurality of display zones including a tabs zone on the first display comprising a plurality of tabs each directed to a distinct subject, wherein selection of one of the plurality of tabs by the operator causes subject specific and scan specific information to be displayed on the first and second displays. The plurality of display zones also includes a task list zone on the first display that is configured to display all steps in a CT scan for a subject selected via a tab in the tabs zone and enable operator selection of a particular step, settings and scanning zones on the first display that are configured to display the subject specific and scan specific information for a respective subject whose tab is selected and a respective step selected in the task list zone, and a post-processing zone on the second display that is configured to enable the operator to manage post-processing set-up, monitoring, and transferring tasks for a CT scan that has been performed. The plurality of distinct display zones on the first and second displays enable the operator to perform workflows on multiple subjects and enable simultaneous usage of the first display and the second display by multiple operators.

According to yet another embodiment of the invention, a CT imaging system includes a rotatable gantry having a gantry opening to receive a subject to be scanned, a high frequency electromagnetic energy projection source configured to project a high frequency electromagnetic energy beam toward the subject, a detector array configured to detect high frequency electromagnetic energy passing through the subject and generate a detector output responsive thereto, a data acquisition system (DAS) connected to the detector array and configured to receive the detector output, and an image reconstructor connected to the DAS and configured to reconstruct one or more images of the subject from the detector output received by the DAS. The CT imaging system also includes a user interface configured to be usable by an operator to set scan related parameters and perform scan related tasks and observe the one or more reconstructed images generated by the image reconstructor, with the user interface further including a first display configured to enable the operator to perform set-up and scanning tasks for one or more patients including acquiring and verifying scan image data and a second display configured to enable the operator to perform image post-processing tasks including reconstructions and reformats. Each of the first display and the second display are configured to display a plurality of distinct display zones thereon, with each of the plurality of display zones being dedicated to a specified task associated with a CT scanning process of the subjects.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A user interface for a computed tomography (CT) imaging system, the user interface comprising:
    a first display configured to enable an operator to perform set-up and scanning tasks associated with performing a CT exam on one or more patients, the set-up and scanning tasks including acquiring and verifying scan image data; and
    a second display configured to enable the operator to perform image post-processing tasks associated with the CT exams on the one or more patients, the image post-processing tasks including performing image reconstructions and reformats;
    wherein each of the first display and the second display are configured to display a plurality of distinct display zones thereon, with the first display including an exam set-up and protocol selection zone configured to enable the operator to select a scan protocol from a protocol list area for performing a CT scan on a desired patient; and
    wherein each of the first display and the second display are operable independent from one another to provide for parallel workflows between the first display and second display and between the patient set-up and scanning tasks and the post-processing tasks.

2. The user interface of claim 1 wherein the plurality of display zones comprises a tabs zone on the first display that includes a plurality of tabs each directed to a distinct patient, wherein each of the plurality of tabs is configured to be selectable by the operator to cause patient specific and scan specific information for a respective patient to be displayed on the first and second displays, and so as to allow for the operator to switch between exam activities related to the patients.

3. The user interface of claim 2 wherein each of the plurality of tabs is configured to indicate a status of an exam for its respective patient, wherein the status comprises one of: not yet scanned, ready to be scanned, and done scanning.

4. The user interface of claim 2 wherein the status further comprises one of: no processing, processing occurring, and done processing.

5. The user interface of claim 2 wherein the plurality of display zones comprises a settings zone on the first display that is configured to display the patient specific and scan specific information for a respective patient whose tab is selected, the patient specific and scan specific information including a plurality of scan settings therein.

6. The user interface of claim 5 wherein the settings zone is configured to highlight scan settings that have been altered from an original protocol setting value, so as to distinguish the altered scan settings from unaltered scan settings.

7. The user interface of claim 2 wherein the plurality of display zones comprises a post-processing zone on the second display that is configured to enable the operator to manage post-processing set-up, monitoring, and transferring tasks.

8. The user interface of claim 7 wherein the plurality of display zones comprises a file manager zone on the second display that is configured to display a list of all current patient exams and any stored prior patient exams, the file manager zone enabling operator selection of a desired patient exam.

9. The user interface of claim 7 wherein the post-processing zone is configured to display post-processing parameters and processing status for a patient selected via either the tabs zone or the file manager zone.

10. The user interface of claim 2 wherein the plurality of display zones comprises a task list zone on the first display configured to display all steps of a CT exam for a patient selected via a tab in the tabs zone, so as to allow the operator to prepare, plan, and optimize the exam.

11. A user interface for a computed tomography (CT) imaging system, the user interface comprising:
a first display configured to enable an operator to perform set-up and scanning tasks associated with performing a CT exam on one or more patients; and
a second display configured to enable the operator to perform image post-processing tasks associated with the CT exams on the one or more patients;
wherein each of the first display and the second display are configured to display a plurality of distinct display zones thereon, the plurality of display zones comprising:
a tabs zone on the first display comprising a plurality of tabs each directed to a distinct subject, wherein selection of one of the plurality of tabs by the operator causes subject specific and scan specific information to be displayed on the first and second displays;
a task list zone on the first display that is configured to display all steps in a scan protocol selected from a protocol list area for performing a CT scan on a subject selected via a tab in the tabs zone and enable operator selection of a particular step;
settings and scanning zones on the first display that are configured to display the subject specific and scan specific information for a respective subject whose tab is selected and a respective step selected in the task list zone; and
a post-processing zone on the second display that is configured to enable the operator to manage post-processing set-up, monitoring, and transferring tasks for a CT scan that has been performed;
wherein the plurality of distinct display zones on the first and second displays enable the operator to perform workflows on multiple subjects and enable simultaneous usage of the first display and the second display by multiple operators.

12. The user interface of claim 11 wherein each of the plurality of tabs is configured to indicate a status of an exam for its respective patient, and further indicate a status of any ongoing processing associated with the exam for the respective patient.

13. The user interface of claim 11 wherein the settings and scanning zones are configured to:
enable the operator to set values for a plurality of scan parameters associated with a CT scan to be performed on a respective subject; and
highlight scan parameters that have been altered from an original protocol parameter value, so as to distinguish the altered scan parameters from unaltered scan parameters.

14. The user interface of claim 11 wherein the plurality of display zones comprises a file manager zone on the second display that is configured to display a list of all current patient exams and any stored prior patient exams, the file manager zone enabling operator selection of a desired patient exam.

15. The user interface of claim 14 wherein the post-processing zone is configured to display post-processing parameters and processing status for a patient selected via either the tabs zone or the file manager zone, the post-processing parameters and processing status being associated with image reconstructions and image reformats.

16. A computed tomography (CT) imaging system comprising:
a rotatable gantry having a gantry opening to receive a subject to be scanned;
a high frequency electromagnetic energy projection source configured to project a high frequency electromagnetic energy beam toward the subject;
a detector array configured to detect high frequency electromagnetic energy passing through the subject and generate a detector output responsive thereto;
a data acquisition system (DAS) connected to the detector array and configured to receive the detector output;
an image reconstructor connected to the DAS and configured to reconstruct one or more images of the subject from the detector output received by the DAS; and
a user interface configured to be usable by an operator to set scan related parameters and perform scan related tasks and observe the one or more reconstructed images generated by the image reconstructor;
wherein the user interface comprises:
a first display configured to enable the operator to perform set-up and scanning tasks for one or more patients including acquiring and verifying scan image data; and
a second display configured to enable the operator to perform image post-processing tasks including reconstructions and reformats;
wherein each of the first display and the second display are configured to display a plurality of distinct display zones thereon, with each of the plurality of display zones being dedicated to a specified task associated with a CT scanning process of the subjects: and
wherein the plurality of distinct display zones includes an exam set-up and protocol selection zone on the first display configured to enable the operator to select a scan protocol from a protocol list area for performing a CT scan on a desired patient.

17. The CT imaging system of claim 16 wherein the plurality of display zones comprises a tabs zone on the first display that includes a plurality of tabs each directed to a distinct subject, wherein each of the plurality of tabs is configured to be selectable by the operator to cause subject specific and scan specific information for a respective subject to be displayed on the first and second displays, and so as to allow for the operator to switch between exam activities related to the subjects.

18. The CT imaging system of claim 16 wherein the plurality of display zones comprises a settings zone on the first display that is configured to display the subject specific and scan specific information for a respective subject whose tab is selected, the subject specific and scan specific information including a plurality of scan settings therein for the selected scan protocol, the settings zone is configured to highlight scan settings that have been altered from an original protocol setting value, so as to distinguish the altered scan settings unaltered scan settings.

19. The CT imaging system of claim 16 wherein the plurality of display zones comprises:
a post-processing zone on the second display that is configured to enable the operator to manage post-processing set-up, monitoring, and transferring tasks; and
a file manager zone on the second display that is configured to display a list of all current subject exams and any stored prior subject exams;

wherein the post-processing zone is configured to display post-processing parameters and processing status for a subject selected via either the tabs zone or the file manager zone.

\* \* \* \* \*